(12) United States Patent
Schmaus et al.

(10) Patent No.: US 8,476,318 B2
(45) Date of Patent: Jul. 2, 2013

(54) POLYETHYLENE GLYCOL ESTERS AND COSMETIC AND/OR DERMATOLOGICAL PREPARATIONS

(75) Inventors: Gerhard Schmaus, Höxter-Bosseborn (DE); Sabine Lange, Holzminden (DE); Rolf Ohrmann, Tostedt (DE); Martina Issleib, Hoisdorf (DE)

(73) Assignee: Symrise AG, Holzminden (DE)

( * ) Notice: Subject to any disclaimer, the term of this patent is extended or adjusted under 35 U.S.C. 154(b) by 593 days.

(21) Appl. No.: 12/596,690

(22) PCT Filed: Apr. 9, 2008

(86) PCT No.: PCT/EP2008/054266
§ 371 (c)(1),
(2), (4) Date: Feb. 23, 2010

(87) PCT Pub. No.: WO2008/128892
PCT Pub. Date: Oct. 30, 2008

(65) Prior Publication Data
US 2010/0150854 A1    Jun. 17, 2010

Related U.S. Application Data

(60) Provisional application No. 60/907,916, filed on Apr. 23, 2007.

(51) Int. Cl.
*A61K 31/22* (2006.01)

(52) U.S. Cl.
USPC ............ 514/546; 560/263; 560/264; 514/547

(58) Field of Classification Search
CPC ................................ A61K 31/215; C07C 69/34
See application file for complete search history.

(56) References Cited

U.S. PATENT DOCUMENTS

| | | | |
|---|---|---|---|
| 5,618,863 A * | 4/1997 | D'Errico et al. ................. | 524/91 |
| 6,432,912 B1 | 8/2002 | Rodelet | |
| 2006/0008850 A1 | 1/2006 | Riggs-Sauthier et al. | |
| 2006/0120642 A1 | 6/2006 | Hirata et al. | |

FOREIGN PATENT DOCUMENTS

| | | |
|---|---|---|
| DE | 1617445 A1 | 3/1972 |
| EP | 0272927 A2 | 6/1988 |
| EP | 1081126 A2 | 3/2001 |
| EP | 1537847 A1 | 6/2005 |
| JP | 2006057070 | 3/2006 |
| WO | WO-2008023338 A1 | 2/2008 |

OTHER PUBLICATIONS

Database Caplus [Online] Chemical Abstracts Service, Columbus, Ohio, US; Fauli, C. et al: "Contribution to the study of PEG derivatives of perlargonic and isostearic acids", XP002493495 retrieved from STN Database accession No. 1976: 107430 abstract.
Ciencia & Industria Farmaceutica, 7(11), 344-51 Coden; CIDFA8; ISSN: 0210-0819, 1975, XP009104915, p. 347; figure 3, p. 349, col. 1, last paragraph.
Weil, J.K. et al.: "Nonionic Wetting Agents", Journal of the American Oil Chemists' Society, vol. 56, No. 9, 1979, pp. 873-877, XP002493461, p. 874; table II; compounds 5, 6, 7.
Parris, N. et al.: "Determination of Diester Formation in Diethylene Glycol and Tetraethylene Glycol Monoesters", Journal of the American Oil Chemists' Society, vol. 56, No. 8, 1979, p. 775, XP002493462, table I.
Database Caplus [Online] Chemical Abstracts Service, Columbus, Ohio, US; Komatsu, Youji et al: "Synthesis and properties of glycol diesters of branched alkanoic acids", XP002493464 retrieved from STN Database accession No. 1975: 3733 abstract.
Maruzen Sekiyu Giho, (18), 47-56 Coden: MSGIB9; ISSN: 0285-4961, 1973, XP002960756, p. 55, compound S8.
Database Caplus [Online] Chemical Abstracts Service, Columbus, Ohio, US; Ichitani, Motokuni et al: "Alkylene glycol dialkanoate plasticizers appropriate volatility for polyvinyl acetals, and their applications", XP002493465, retrieved from STN, Database accession No. 2006: 189880 abstract, 2006.
Aiken, W. et al.: "Creep Behavior of Plasticized Vinylite VYNW*", Journal of Polymer Science, vol. 2, No. 2, 1947, pp. 178-198, XP002493463 p. 188, paragraph 2.

\* cited by examiner

*Primary Examiner* — Paul A Zucker
(74) *Attorney, Agent, or Firm* — Novak Druce Connolly Bove + Quigg LLP

(57) ABSTRACT

The invention relates to polyethylene glycol esters and blends of the polyethylene glycol esters with polyethylene glycol ethers, together with in particular cosmetic and/or dermatological preparations containing them, methods for the production thereof and use thereof.

15 Claims, No Drawings

POLYETHYLENE GLYCOL ESTERS AND COSMETIC AND/OR DERMATOLOGICAL PREPARATIONS

CROSS-REFERENCE TO RELATED APPLICATIONS

This application claims benefit of priority to PCT/EP2008/054266, filed on Apr. 9, 2008, which asserts priority to U.S. Provisional Application No. 60/907,916, filed on Apr. 23, 2007, which are incorporated herein by reference in their entireties.

The invention relates to polyethylene glycol esters of the general formula 1 and blends of the polyethylene glycol esters with polyethylene glycol ethers, together with in particular cosmetic and/or dermatological preparations containing them, methods for the production thereof and use thereof.

In the field of cosmetic agents for skin, scalp and hair care, the consumer has a large number of requirements. Sufficient skin fat content and sufficient skin moisture are essential prerequisites for a healthy, dermatologically normal skin. With detergent formulations such as for example shower gels or bath preparations, cleaning and conditioning effects are to the fore. Furthermore, great store is set by such differing parameters as maximum dermatological compatibility, good moisturizing properties, elegant appearance, optimum organoleptic impression and storage stability.

Preparations which in particular are used to clean and condition the human skin, scalp and hair generally contain large amounts of surface-active anionic, nonionic, cationic and/or amphoteric or zwitterionic surfactants. One of the main problems of the regular application of shampoos and bath oil preparations is the dissolving of lipophilic sebum constituents out of the external skin and scalp layers in particular by these surfactant preparations. The consequence is damage to the naturally present skin barrier which, as is known from numerous investigations, is accompanied by a significant increase in transepidermal water loss and consequently in a significant reduction in the water content of the skin or scalp. This ultimately leads to drying of the skin or scalp with undesired accompanying symptoms such as in particular increased pruritus, reddening or flaking.

In order to cope with the increasing requirements of the market in relation to detergent and skin-cleansing cosmetic and dermatological products such as in particular shampoos, bath preparations, cleansing milks, sprayable cleansing emulsions or aqueous, alcoholic or glycolic cleansing fluids, in particular that of ensuring optimum moisturization and thus counteracting drying of the skin by detergent substances, novel oil bodies and emulsifier mixtures are constantly being developed and tested. These are often pure hydrocarbons, ester oils and plant and animal oils/fats/waxes, which are distinguished, however, by only very limited water solubility and thus cannot be incorporated in the amount necessary for moisturization into the stated cosmetic and dermatological preparations.

The following further properties are likewise important for cosmetic and dermatological preparations:

readily solubilizing properties for moderately water-soluble active ingredients, in particular moisturizing and/or skin barrier-repairing active ingredients (in particular fatty oils, long-chain fatty acids, long-chain saturated and unsaturated hydrocarbons such as paraffins, squalene and squalane, ceramides, pseudoceramides, cholesterol and/or phytosterols, antiacne agents, antidandruff agents, antiirritants, deodorants, antioxidants, UV-light protection filters and perfume oils, moderate to good spreading behavior, easy incorporability into current cosmetic and pharmaceutical preparations, good dermatological compatibility, toxicological and ecotoxicological safety, ability to impart a pleasant feeling to the skin.

The above parameters are conventionally not regarded as being of equal weight in cosmetic and dermatological preparations, but rather are weighted differently depending on the field of application of the respective cosmetic and/or dermatological preparation. It was therefore also an object of the present invention to provide substances which are suitable for the various fields of application and fulfil the above parameters and may thus be used in a large number of different cosmetic and/or dermatological preparations.

The object of the present invention was in particular to provide substances which may serve to condition the skin, to reduce, delay or prevent drying out of the skin, to regenerate the skin barrier function, to moisturize the skin and/or to the increase the solubility of a substance which is not water-soluble or is only moderately water-soluble, in particular in cosmetic and/or dermatological formulations. In addition, it was intended to provide methods of producing corresponding substances and uses thereof.

The invention therefore teaches the use of polyethylene glycol esters of the formula 1

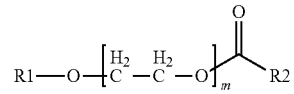

Formula 1 wherein m=3-7 and preferably 5, $R_1$=H or

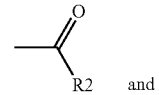

and $R_2$=in each case a branched or unbranched alkyl group, the number of carbon atoms amounting to 8, to a) condition the skin, and/or b) reduce, delay or prevent drying out of the skin, and/or c) regenerate the skin barrier function, and/or d) moisturize the skin.

According to the invention, polyethylene glycol esters of the above formula 1 are additionally provided, wherein the substances poly(oxy-1,2-ethanediyl), α-(1-oxoisooctyl)-ω-hydroxy- (CARN: 127739-58-6); hexanoic acid, 3,5,5-trimethyl-, 2-[2-(2-hydroxyethoxy)ethoxy]ethyl ester (CARN: 7339-81-3), hexanoic acid, 3,5,5-trimethyl-, 2-(2-hydroxyethoxy)ethyl ester (CARN: 7339-80-2) and poly(oxy-1,2-ethanediyl), α-(1-oxononyl)-o-hydroxy- (CARN: 31621-91-7; polyethylene glycol monopelargonate) are already are known as such and accordingly are not claimed as such. These polyethylene glycol esters have hitherto only been described as lubricants for turbines or as educts for the production of specific esters of hydroxynaphthoic acids with polyethylene glycol esters. Their suitability for use in cosmetic or dermatological products was not hitherto known and also not to be expected.

It has now been found that polyethylene glycol mono- and diesters of the formula 1 have excellent skin-conditioning properties, in particular they may reduce, delay or prevent drying out of the skin, and in particular may serve through moisturization in regenerating the skin barrier function. The polyethylene glycol esters of the formula 1 are suitable for use in cosmetic and dermatological preparations with the most varied fields of application; in particular they may be readily incorporated into cosmetic and dermatological preparations, exhibit good dermatological compatibility, are toxicologically and ecotoxicologically safe and impart a particularly pleasant skin feel.

For the purposes of the present invention, "skin" is in particular the organ covering the outside of the human body and consisting of the epidermis, dermis and subcutis. Linings and/or coverings of internal organs, for example mucous membranes, periostea, vascular tissue and the retina are not "skin" for the purposes of the present invention.

"Cosmetic" preparations for the purposes of the present invention are in particular preparations which are suitable for topical application to the skin of a human being, in particular to achieve a cosmetic effect. "Dermatological preparations" are preparations suitable for topical application to the skin of a human being to achieve a pharmaceutical effect, in particular to alleviate or cure a disease, in particular a skin disease.

The polyethylene glycol esters of the formula 1 are producible according to the invention by reacting ethylene oxide with one or a mixture comprising a plurality of branched or unbranched alkyl carboxylic acids, whose number of carbon atoms amounts to 9 (C9 acids). Particularly preferred for the purposes of the present invention are polyethylene glycol mono- and diesters of the formula 1, whose average number of ethylene oxide units amounts to 5. These polyethylene glycol esters are preferably produced by reacting 5 mol of ethylene oxide with 1 mol of C9 acids. Particularly preferred C9 acids for producing the polyethylene glycol esters of the formula 1 are 3,5,5-trimethylhexanoic acid (CARN: 3302-10-1), isononanoic acid (CARN: 26896-18-4) and blends of these acids. The polyethylene glycol esters according to the invention may be produced using common synthesis methods, such as those described inter alia by H. Beyer and W. Walter in Lehrbuch der Organischen Chemie (Hirzel Verlag, Stuttgart, 1988, ISBN: 3-7776-0438-0).

According to the invention, the polyethylene glycol esters of the formula 1 are preferably not used as pure substances, but instead as mixtures of two or more polyethylene glycol mono- and/or diesters. Such mixtures are advantageously obtained with the above-described production of polyethylene glycol esters. The average number of ethylene oxide units and the amount ratios of polyethylene mono- to diesters may in each case be adjusted by appropriate selection of the molar amounts of ethylene oxide and carboxylic acid (N). The blends arising during such reactions may contain small amounts of non-moisturizing polyethylene glycols; however, these do not disrupt the advantageous effects of the invention, in particular the suitability of the polyethylene glycol esters according to the invention for conditioning the skin, for reducing, delaying or preventing drying out of the skin, for regenerating the skin barrier function, for moisturizing the skin, and/or their general usability in cosmetic and/or dermatological preparations.

Particular preference is given according to the invention to those preparations which are characterized in that the ratio of the total mass of all polyethylene glycol esters of the formula 1, in which only one of the residues $R_1$ and $R_2$ is H, to the total mass of all polyethylene glycol esters of the formula 1, in which the residues $R_1$ and $R_2$ are not H, is 4:1 to 1:3, preferably 3:1 to 1:2 and most preferably 2:1 to 1:1. The above-stated properties and advantages a)-d) of the polyethylene glycol esters of the formula 1 come particularly into their own in those preparations in which the ratio of the total mass of all polyethylene glycol monoesters of the formula 1 with $R_1$=H, $R_2$ is not H and m=5 to the total mass of polyethylene glycol diesters of the formula 1 with $R_1$ and $R_2$ is not H and m=5 is 2:1 to 1:1, particularly preferably 1.8:1 to 1.2:1.

According to the invention, polyethylene glycol esters of the formula 1 are preferably used in preparations together with one or more polyethylene glycol ethers of the formula 2,

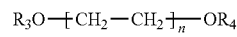

Formula 2 wherein n=7-30 and preferably 9, and $R_3$ and $R_4$ in each case, mutually independently, mean H or a saturated or unsaturated, branched or unbranched alkyl group, in which the number of carbon atoms amounts to 10-15. It has surprisingly been found that blends of one or more polyethylene glycol esters of the formula 1 with polyethylene glycol ether(s) of the formula 2, in particular in aqueous preparations and therein in turn in particular in aqueous preparations with a low surfactant content, in particular a total content of 5-20 wt. % of nonionic, cationic, amphoteric and zwitterionic surfactants, advantageously give rise to elevated solubility of the polyethylene glycol esters of the formula 1 in the preparations.

According to the invention, preparations are accordingly also provided which contain one or more polyethylene glycol esters of the formula 1, wherein m=3-7 and preferably 5, $R_1$=H or

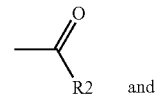

and $R_2$=in each case a branched or unbranched alkyl group, whose number of carbon atoms amounts to 8, and one or more polyethylene glycol ethers of the formula 2, wherein n=7 to 30 and preferably 9 and $R_3$ and $R_4$ in each case, mutually independently, mean H or a saturated or unsaturated, branched or unbranched alkyl group, in which the number of carbon atoms preferably amounts to 10 to 15 and preferably 13.

According to the invention, the polyethylene glycol ethers of the formula 2 are preferably produced by reacting ethylene oxide with one or a mixture of a plurality of saturated or unsaturated, branched or unbranched primary alcohols, whose number of carbon atoms amounts to 11-16. A particularly preferred alcohol is tridecan-1-ol. It is likewise particularly preferred to react the primary alcohol(s) (in particular tridecan-1-ol) with 9 mol of ethylene oxide per mol (total) of primary alcohols. Such polyethylene glycol ethers of the formula 2 have proven to be particularly suitable for blending with polyethylene glycol esters of the formula 1 and in particular for increasing the solubility thereof in aqueous and in particular low-surfactant aqueous preparations. Like the polyethylene glycol esters of the formula 1, the polyethylene glycol ethers of the formula 2 are also preferably used as ether mixtures; such ether mixtures are obtainable in an advantageously simple manner with the production method described above.

Blends of the polyethylene glycol esters of the formula 1 with one or more polyethylene glycol ethers of the formula 2 are particularly suitable for use above all in aqueous, surfactant products for conditioning and cleansing the skin (e.g. shampoos, bath preparations, cleansing milk, sprayable cleansing emulsions or aqueous, alcoholic or glycolic cleansing fluids). By adding the readily watersoluble polyethylene glycol ethers of the formula 2, it is particularly readily possible to use the polyethylene glycol esters with excellent moisturizing properties of the formula 1 in the amount in aqueous, surfactant preparations and in particular cosmetic preparations which is necessary in order sufficiently to counteract the defatting and skin- and scalp-drying effect of surfactant cleansing products.

Human in vivo investigations have unambiguously demonstrated the antidehydrating effect described here of the preparations according to the invention, which counteracts drying out of the skin and scalp and which is attributable in particular to the skin- and scalp-moisturizing property thereof. More detailed explanations of the invention are provided in the Examples.

It has also surprisingly been found that the preparations according to the invention containing polyethylene glycol esters of the formula 1 and polyethylene glycol ethers of the formula 2 have excellent solubilizing properties with regard to further, only moderately water-soluble, lipophilic substances or substance mixtures such as for example perfume oils, antidandruff agents, antiacne agents or substances regenerating the skin barrier. In particular, the very good solubility mediating properties of the blends according to the invention with regard to sebum- and skin barrier-regenerating active ingredients such as for example fatty oils, fatty acids, ceramides, pseudoceramides, sterols, phytosterols or hydrocarbons ideally suit them to use in cosmetic and dermatological agents for cleansing and conditioning skin and scalp, in particular for regenerating the skin barrier damaged by surfactants and consequently for protecting the skin from drying out.

Preparations or blends according to the invention containing polyethylene glycol esters of the Formula 1 and polyethylene glycol ethers of the formula 2 may conventionally be used in an amount of 0.1-50 wt. % in cosmetic and dermatological preparations. Preference is given to input amounts of from 0.5-20 wt. %, with input amounts of from 1-10 wt. % being very particularly preferred. The polyethylene glycol esters according to the invention of the formula 1 and the polyethylene glycol ethers of the formula 2 are used in the blends according to the invention in an amount ratio range of polyethylene glycol ester:polyethylene glycol ether of from 90 wt. %:10 wt. % to 10 wt. %:90 wt. %, and preferably in an amount ratio range of from 75 wt. %:25 wt. % to 25 wt. %:75 wt. %.

In a particularly preferred development of the invention, a preparation according to the invention resulting from the reaction of 1 mol of 3,5,5-trimethylhexanoic acid with 5 mol of ethylene oxide has the following composition: a total of 44% polyethylene glycol mono-3,5,5-trimethylhexanoate with an average ethylene oxide number of 5 ethylene oxide units and a total of 48% polyethylene glycol di-3,5,5-trimethylhexanoate with an average ethylene oxide number of 5 ethylene oxide units. In addition, the product contains 8% of non-alkylated polyethylene glycols which consequently do not have a moisturizing action. The exact amount ratios of the polyethylene glycol mono- and diesters, determined by gas chromatography, may be found in Table 1.

TABLE 1

GC analysis of the reaction product from reacting 1 mol of 3,5,5-trimethylhexanoic acid (CARN: 3302-10-1) with 5 mol of ethylene oxide; GC conditions: 30 m DB-1 GC column; temperature program: initial temperature: 80° C., temperature program 8° C./min, final temperature 320° C., FID detection (FID = flame ionization detector).

| Retention time [min] | Retention index | GC area percent | Substance |
|---|---|---|---|
| 1.47 | 941 | 0.48 | diethylene glycol |
| 2.98 | 1139 | 0.43 | 3,5,5-trimethylhexanoic acid |
| 3.43 | 1183 | 0.74 | triethylene glycol |
| 5.33 | 1355 | 0.57 | monoethylene glycol mono-3,5,5-trimethylhexanoate |
| 6.23 | 1436 | 1.95 | tetraethylene glycol |
| 8.02 | 1601 | 2.02 | diethylene glycol mono-3,5,5-trimethylhexanoate |
| 9.08 | 1704 | 2.47 | pentaethylene glycol |
| 10.70 | 1871 | 6.97 | triethylene glycol mono-3,5,5-trimethylhexanoate |
| 11.67 | 1978 | 2.07 | hexaethylene glycol |
| 11.82 | 1995 | 0.41 | monoethylene glycol di-3,5,5-trimethylhexanoate |
| 13.06 | 2139 | 9.92 | tetraethylene glycol mono-3,5,5-trimethylhexanoate |
| 13.97 | 2252 | 1.65 | heptaethylene glycol |
| 14.17 | 2277 | 1.94 | diethylene glycol di-3,5,5-trimethylhexanoate |
| 15.16 | 2405 | 8.84 | pentaethylene glycol mono-3,5,5-trimethylhexanoate |
| 16.17 | 2543 | 5.96 | triethylene glycol di-3,5,5-trimethylhexanoate |
| 17.06 | 2670 | 6.56 | hexaethylene glycol mono-3,5,5-trimethylhexanoate |
| 17.97 | 2808 | 7.09 | tetraethylene glycol di-3,5,5-trimethylhexanoate |
| 18.80 | 2937 | 5.06 | heptaethylene glycol mono-3,5,5-trimethylhexanoate |
| 19.61 | 3070 | 5.89 | pentaethylene glycol di-3,5,5-trimethylhexanoate |
| 20.39 | 3201 | 2.38 | octaethylene glycol mono-3,5,5-trimethylhexanoate |
| 21.13 | 3332 | 5.27 | hexaethylene glycol di-3,5,5-trimethylhexanoate |
| 21.86 | 3466 | 0.76 | nonaethylene glycol mono-3,5,5-trimethylhexanoate |
| 22.55 | 3597 | 6.79 | heptaethylene glycol di-3,5,5-trimethylhexanoate |
| 23.87 | 3860 | 6.59 | octaethylene glycol di-3,5,5-trimethylhexanoate |
| 25.10 | 4122 | 4.69 | nonaethylene glycol di-3,5,5-trimethylhexanoate |
| 26.26 | 4383 | 2.51 | decaethylene glycol di-3,5,5-trimethylhexanoate |

The preferably cosmetic and dermatological preparations according to the invention containing polyethylene glycol esters of the formula 1 and polyethylene glycol ethers of the formula 2 particularly preferably comprise surfactant formulations for skin, scalp and hair care, such as in particular bath and shower foams, hair shampoos and conditioners for hair and scalp care together with skin-cleansing bath preparations. The polyethylene glycol esters of the formula 1 are preferably used in preparations with a total surfactant content of 2-wt. %, preferably of 5-20 wt. % relative to the total preparation used.

The preparations according to the invention may also be of additional benefit to cosmetic and dermatological products such as for example water-, alcohol- or glycol-based creams, sprayable emulsions, cleansing milks, cleansing lotions as well as further dermatological and cosmetic administration forms for skin, scalp and hair care in that they moisturize the skin and scalp and regenerate the damaged skin barrier. The preparations according to the invention may be furthermore also be formulated as emulsions of the "water-in-oil" (W/O)

or "oil-in-water" (O/W) type, or as multiple emulsions, e.g. of the water-in-oil-in-water (W/O/W), PIT emulsion, Pickering emulsion, microemulsion or nanoemulsion type; particularly preferred emulsions are of the "oil-in-water" (O/W) or the water-in-oil-in-water (W/O/W) type. The preparations according to the invention may also in particular be formulated as a pencil, stick, aerosol, spray, foam, impregnation solution e.g. for cosmetic tissues, cleansing agents such as for example soap, syndets, skin care product, cream, lotion, milk, emulsion foam, micro- or nanoemulsion, paste, gel (e.g. hydro- or hydrodispersion gel), balsam, serum, roll-on, pump spray, aerosol (foaming, non-foaming or post-foaming), skin care product, foot care product (including keratolytic agents, deodorants), insect repellent, sunscreen preparation, aftersun preparation, shaving preparation, depilatory product, hair care product such as for example shampoo, 2-in-1 shampoo, antidandruff shampoo, baby shampoo, shampoo for dry scalp, shampoo concentrate, conditioner, hair tonic, hair lotion, hair rinse, hair cream, permanent wave and setting lotion, hair smoothing product (defrizzing agent, relaxer), hair strengthener (spray), styling aid (e.g. gel), as a blonding product, hair lightener, hair conditioner, hair mousse, hair toning product, deodorant and/or antiperspirant; mouthwash and water pick, aftershave balm, pre- and aftershave lotion, eye care cream, make-up, make-up remover, baby product, bath product (e.g. capsule), or face mask.

Surfactant substances and emulsifiers, which, due to their solubilizing properties, may contribute to a reduction in sebum concentration, to drying out of the skin and to water loss from the skin and/or may damage the skin barrier, and which may be contained in preparations according to the invention, in particular cosmetic and/or dermatological preparations, are listed below.

Surfactants

The surface-active substances which may be contained are anionic, nonionic, cationic and/or amphoteric or zwitterionic surfactants. Surfactant-containing cosmetic preparations, such as for example shower gels, bath foams, shampoos etc., preferably contain at least one anionic surfactant. The surfactant content is here conventionally approx. 0.1 to 50, preferably 2 to 30 and in particular 5 to wt. %. Typical examples of anionic surfactants are soaps, alkyl benzene sulfonates, alkane sulfonates, olefin sulfonates, alkyl ether sulfonates, glycerol ether sulfonates, alpha-methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and the salts thereof, fatty acid isethionates, fatty acid sarcosinates, fatty acid taurides, N-acylamino acids, such as for example acyl lactylates, acyl tartrates, acyl glutamates and acyl aspartates, alkyl oligoglucoside sulfates, protein fatty acid condensation products (in particular wheat-based plant products) and alkyl (ether) phosphates. If the anionic surfactants contain polyglycol ether chains, these may exhibit a conventional, but preferably a narrowed homolog distribution. Typical examples of nonionic surfactants are fatty alcohol polyglycol ethers, alkyl phenol polyglycol ethers, fatty acid polyglycol esters, fatty acid amide polyglycol ethers, fatty amine polyglycol ethers, alkoxylated triglycerides, mixed ethers or mixed formals, optionally partially oxidized alk(en)yl oligoglycosides or glucoronic acid derivatives, fatty acid N-alkylglucamides, protein hydrolysates (in particular wheat-based plant products), polyol fatty acid esters, sugar esters, sorbitan esters, polysorbates and amine oxides. If the nonionic surfactants contain polyglycol ether chains, these may exhibit a conventional, but preferably a narrowed homolog distribution. Typical examples of cationic surfactants are quaternary ammonium compounds, such as for example dimethyldistearylammonium chloride, and ester quats, in particular quaternized fatty acid trialkanolamine ester salts. Typical examples of amphoteric or zwitterionic surfactants are alkyl betaines, alkylamidobetaines, aminopropionates, aminoglycinates, imidazolinium betaines and sulfobetaines. The stated surfactants are exclusively known compounds.

Emulsifiers

Emulsifiers which may be used are for example nonionogenic surfactants from at least one of the following groups: addition products of 2 to 30 mol of ethylene oxide and/or 0 to 5 mol of propylene oxide onto alkylamines with 8 to 22 carbon atoms in the alkyl residue, alkyl oligoglycosides with 8 to 22 carbon atoms in the alkyl residue. Addition products of 15 to 60 mol ethylene oxide onto castor oil and/or hardened castor oil. Partial esters of glycerol and/or sorbitan with unsaturated, linear or saturated, branched fatty acids having 12 to 22 carbon atoms and/or hydroxycarboxylic acids having 3 to 18 carbon atoms. Partial esters of polyglycerol (average intrinsic degree of condensation 2 to 8), polyethylene glycol (molecular weight 400 to 5000), trimethylolpropane, pentaerythritol, sugar alcohols (for example sorbitol), alkyl glucosides (for example methyl glucoside, butyl glucoside, lauryl glucoside) and polyglucosides (for example cellulose) with saturated and/or unsaturated, linear or branched fatty acids having 12 to 22 carbon atoms and/or hydroxycarboxylic acids having 3 to 18 carbon atoms. Mixed esters prepared from pentaerythritol, fatty acids, citric acid and fatty alcohol and/or mixed esters prepared from fatty acids having 6 to 22 carbon atoms, methyl glucose and polyols, preferably glycerol or polyglycerol. Mono-, di- and trialkyl phosphates and mono-, di- and/or tri-PEG alkyl phosphates and the salts thereof, wool wax alcohols, polysiloxane/polyalkyl/polyether copolymers or corresponding derivatives, block copolymers for example polyethylene glycol-30 dipolyhydroxystearates, polymer emulsifiers, for example Pemulen grades (TR-1, TR-2) from Goodrich, polyalkylene glycols and glycerol carbonate.

Sorbitan Esters

Possible sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof.

Polyglycerol Esters

Typical examples of suitable polyglycerol esters are polyglyceryl-2 dipolyhydroxystearate, polyglycerol-3 diisostearate, polyglyceryl-4 isostearate, polyglyceryl-3 oleate, diisostearoyl polyglycerol-3 diisostearate, polyglyceryl-3 methyl glucose distearate, polyglyceryl-3 beeswax, polyglyceryl-4 caprate, polyglyceryl-3 cetyl ether, polyglyceryl-3 distearate and polyglyceryl polyricinoleate, polyglyceryl dimerate isostearate and mixtures thereof.

Anionic Emulsifiers

Typical anionic emulsifiers are aliphatic fatty acids having 12 to 22 carbon atoms, such as for example palmitic acid, stearic acid or behenic acid, and dicarboxylic acids having 12 to 22 carbon atoms, such as for example azelaic acid or sebacic acid.

Amphoteric and Cationic Emulsifiers

In addition, zwitterionic surfactants may be used as emulsifiers. Zwitterionic surfactants are those surface-active compounds which bear at least one quaternary ammonium group and at least one carboxylate and one sulfonate group per molecule. Particularly suitable zwitterionic surfactants are the so-called betaines such as N-alkyl-N,N-dimethylammonium glycinates, for example cocoalkyl dimethylammonium glycinate, N-acylaminopropyl-N,N-dimethylammonium glycinates, for example cocoacylaminopropyl dimethylammonium glycinate, and 2-alkyl-3-carboxylmethyl-3-hydroxyethyl imidazolines with in each case 8 to 18 C atoms in the alkyl or acyl group and cocoacylaminoethylhydroxyethylcarboxymethyl glycinate. Particular preference is given to the fatty acid amide derivative known by the CTFA name cocamidopropyl betaine. Ampholytic surfactants are likewise suitable emulsifiers. Ampholytic surfactants are understood to be those surface-active compounds which, in addition to one C8/18-alkyl or acyl group per molecule, contain at least one free amino group and at least one —COOH or —SO$_3$H group and are capable of forming internal salts. Examples of suitable ampholytic surfactants are N-alkylglycines, N-alkylpropionic acids, N-alkylaminobutyric acids, N-alkyliminodipropionic acids, Nhydroxyethyl-N-alkylamidopropylglycines, N-alkyltaurines, N-alkylsarcosines, 2-alkylaminopropionic acids and alkylaminoacetic acids with in each case approx. 8 to 18 C atoms in the alkyl group. Particularly preferred ampholytic surfactants are N-cocoalkylaminopropionate, cocoacylaminoethylaminopropionate and C12/18-acylsarcosine. Finally, cationic surfactants may also be considered as emulsifiers, with those of the ester quat type, preferably methyl-quaternized difatty acid triethanolamine ester salts, being particularly preferred.

Depending on the intended application, the polyethylene glycol esters of the formula 1 and in particular the preparations according to the invention containing at least one polyethylene glycol ester of the formula 1 and at least one polyethylene glycol ether of the formula 2 may also contribute to increasing the dissolution behavior of further auxiliary substances and additives or cosmetic and dermatological active ingredients contained in the cosmetic formulations, such as for example oil bodies which are water-soluble only to a certain extent, pearlescent waxes, consistency providers, thickeners, stabilizers, silicone compounds, fats, waxes, lecithins, phospholipids, biogenic active ingredients, UV sun protection factors, antioxidants, (for example vitamin C and derivatives, tocopherols and derivatives, vitamin A and derivatives), 2-hydroxycarboxylic acids (for example citric acid, malic acid, L-, D- or DL-lactic acid), antiirritants, substances which accelerate wound healing, antiaging products (for example collagen stimulators and matrix metalloproteinase inhibitors), skin-conditioning agents (for example cholesterol, phytosterols, free fatty acids, ceramides, pseudoceramides, waxes), softening, moistening and/or moisture-retaining substances (in particular glycerol, urea or 1,2-alkane diols such as 1,2-pentanediol, 1,2-hexanediol, 1,2-octanediol and/or 1,2-decanediol), saturated fatty acids, mono- or polyunsaturated fatty acids, alpha-hydroxy acids, polyhydroxyfatty acids or the derivatives thereof (for example linoleic acid, alpha-linolenic acid, gamma-linolenic acid or arachidonic acid and the respective natural or synthetic esters thereof), waxes, ceramides, pseudoceramides, cholesterol, phytosterols, or other conventional constituents of a cosmetic or dermatological preparation such as further alcohols, polyols, deodorants (for example farnesol, veticol, ethylhexylglycerin, 1,2-decanediol), antiperspirants, anti-dandruff agents (for example climbazole, ketoconazole, piroctone olamine, zinc pyrithione), antiacne active ingredients, film formers, insect repellents, self-tanning agents and biological skin tanning agents, skin-lightening active ingredients (depigmenting agents, (for example tyrosinase inhibitors), hydrotropes, preservatives, bactericides, fungicides, virucides, cooling active ingredients, perfume oils, dyes etc.

Further such substances are listed below by way of example, wherein the list of substances whose dissolution behavior is influenced by the preparations according to the invention, in particular the polyethylene glycol ester- and polyethylene glycol ether-containing preparations according to the invention, may advantageously be extended by further active ingredients of comparable polarity.

Oil Bodies

Bodycare products advantageously contain a series of further oil bodies and emollients, which may contribute to further optimization of the properties of the polyethylene glycol esters of formula 1 and in particular of the preparations according to the invention containing at least one polyethylene glycol ester of the formula 1 and at least one polyethylene glycol ether of the formula 2. The oil bodies are conventionally present in a total amount of 0.1-50 wt. %, preferably 1-wt. % and in particular 2-10 wt. % relative in each case to the overall preparation. The oil bodies may particularly preferably take the form of Guerbet alcohols based on fatty alcohols having 6 to 18, preferably 8 to 10 carbon atoms; also possible are esters of linear C6-C22 fatty acids with linear or branched C6-C22 fatty alcohols or esters of branched C6-C13 carboxylic acids with linear or branched C6-C22 fatty alcohols, such as for example myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear C6-C22 fatty acids with branched alcohols, in particular 2-ethylhexanol and 3,5,5-trimethylhexanol, esters of C18-C38 alkylhydroxycarboxylic acids with linear or branched C6-C22 fatty alcohols, in particular dioctyl malates, esters of linear and/or branched fatty acids with polyhydric alcohols (such as for example propylene glycol, dimeric diol or trimeric triol) and/or Guerbet alcohols, triglycerides based on C6-C10 fatty acids, liquid mono-/di-/triglyceride mixtures based on C6-C18 fatty acids, esters of C6-C22 fatty alcohols and/or Guerbet alcohols with aromatic carboxylic acids, in particular benzoic acid, esters of C2-C12 dicarboxylic acids with linear or branched alcohols having 1 to 22 carbon atoms or polyols having 2 to 10 carbon atoms and 2 to 6 hydroxyl groups, plant oils, branched primary alcohols, substituted cyclohexanes, linear and branched C6-C22 fatty alcohol carbonates, such as for example dicaprylyl carbonates, Guerbet carbonates based on fatty alcohols with 6 to 18, preferably 8 to 10 C atoms, esters of benzoic acid with linear and/or branched C6-C22 alcohols, linear or branched, symmetrical or asymmetrical dialkyl ethers having 6 to 22 carbon atoms per alkyl group, such as for example dicaprylyl ether, ring-opening products of epoxidized fatty acid esters with polyols, silicone oils (cyclomethicones, silicon methicone types etc.) and/or aliphatic or naphthenic hydrocarbons, such as for example squalane, squalene or dialkylcyclohexanes.

Fats and Waxes

Fats and waxes are added to personal hygiene products as conditioning substances and also in order to improve the consistency of the cosmetics. Typical examples of fats are glycerides, i.e. solid or liquid plant or animal products, which substantially consist of higher fatty acid mixed glycerol esters. Fatty acid partial glycerides, i.e. technical mono- and/or diesters of glycerol with fatty acids having 12 to 18 carbon atoms such as for instance glycerol mono/dilaurate, palmitate or stearate are also suitable for this purpose. Possible waxes are inter alia natural waxes, such as for example candelilla wax, carnauba wax, Japan wax, esparto grass wax, cork wax, guaruma wax, rice germ oil wax, sugar cane wax, ouricury wax, montan wax, beeswax, shellac wax, spermaceti, lanolin (wool wax), uropygial fat, ceresin, ozokerite (earth wax), petroleum jelly, paraffin waxes, micro waxes; chemically modified waxes (hard waxes), such as for example montan ester waxes, Sasol waxes, hydrogenated jojoba waxes and synthetic waxes, such as for example polyalkylene waxes. In addition to fats, fat-like substances such as lecithins and phospholipids are also feasible additives. The term lecithins is understood by a person skilled in the art to mean those glycerol phospholipids which are formed by esterification from fatty acids, glycerol, phosphoric acid and choline. Lecithins are therefore also frequently known in specialist circles as phosphatidyl cholines (PC). Examples of natural lecithins include cephalins, which are also known as phosphatidic acids and represent derivatives of 1,2-diacyl-sn-glycerol-3-phosphoric acids. In contrast, phospholipids are usually understood to mean mono- and preferably diesters of phosphoric acid with glycerol (glycerol phosphates), which are general considered to be fats. Sphingosines or sphingolipids may also be considered.

Pearlescent Waxes

Examples of pearlescent waxes are: alkylene glycol esters, specifically ethylene glycol distearate; fatty acid alkanolamides, specifically cocofatty acid diethanol amide; partial glycerides, specifically stearic acid monoglyceride; esters of polyvalent, optionally hydroxy-substituted carboxylic acids with fatty alcohols with 6 to 22 carbon atoms, specifically long-chain esters of tartaric acid; fatty substances, such as for example fatty alcohols, fatty ketones, fatty aldehydes, fatty ethers and fatty carbonates, which comprise in total at least 24 carbon atoms, specifically laurone and distearyl ether; fatty acids such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups and mixtures thereof.

Consistency Providers and Thickeners

Further consistency providers which may primarily be considered are fatty alcohols or hydroxyfatty alcohols having 12 to 22 and preferably 16 to 18 carbon atoms and also partial glycerides, fatty acids or hydroxyfatty acids. Preference is given to a combination of these substances with alkyl oligoglucosides and/or fatty acid N-methylglucamides of identical chain length and/or polyglycerol poly-12-hydroxystearates. Suitable thickeners are for example Aerosil grades (hydrophilic silicas), polysaccharides, in particular xanthan gum, guar, agar-agar, alginates and tyloses, carboxymethylcellulose and hydroxyethyl- and hydroxypropylcellulose, also relatively high molecular weight polyethylene glycol mono- and diesters of fatty acids, polyacrylates, (for example Carbopol™ and Pemulen grades from Goodrich; Synthalene™ from Sigma; Keltrol grades from Kelco; Sepigel grades from Seppic; Salcare grades from Allied Colloids), polyacrylamides, polymers, polyvinyl alcohol and polyvinylpyrrolidone. Bentonites, such as for example Bentone™ gel VS-5PC (Rheox), have also proven particularly effective which comprise a mixture of cyclopentasiloxane, disteardimonium hectorite and propylene carbonate. Also feasible are surfactants, such as for example ethoxylated fatty acid glycerides, esters of fatty acids with polyols such as for example pentaerythritol or trimethylolpropane, fatty alcohol ethoxylates with a narrowed homolog distribution or alkyl oligoglucosides as well as electrolytes such as common salt and ammonium chloride.

Stabilizers

Stabilizers which may be used are metal salts of fatty acids, such as for example magnesium, aluminum and/or zinc stearate or ricinoleate.

Polymers

Suitable cationic polymers are for example cationic cellulose derivatives, such as for example a quaternized hydroxyethylcellulose, which is available under the name Polymer JR 400™ from Amerchol, cationic starch, copolymers of diallyl ammonium salts and acrylamides, quaternized vinylpyrrolidone/vinylimidazole polymers, such as for example Luviquat™ (BASF), condensation products of polyglycol and polyamines, quaternized collagen polypeptides, such as for example lauryldimonium hydroxypropyl hydrolyzed collagen (Lamequat™ L/Grünau), quaternized wheat polypeptides, polyethyleneimine, cationic silicone polymers, such as for example amodimethicones, copolymers of adipic acid and dimethylaminohydroxypropyl diethylenetriamine (Cartaretine™/Sandoz), copolymers of acrylic acid with dimethyldiallylammonium chloride (Merquat™ 550/Chemviron), polyaminopolyamides and the crosslinked water-soluble polymers thereof, cationic chitin derivatives such as for example quaternized chitosan, optionally dispersed in microcrystalline form, condensation products prepared from dihaloalkylene, such as for example dibromobutane with bisdialkyl amines, such as for example bisdimethylamino-1,3-propane, cationic guar gum, such as for example Jaguar™ CBS, Jaguar™ C-17, Jaguar™ C-16 from Celanese, quaternized ammonium salt polymers, such as for example Mirapol™ A-15, Mirapol™ AD-1, Mirapol™ AZ-1 from Miranol.

Examples of feasible anionic, zwitterionic, amphoteric and nonionic polymers are vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and the esters thereof, uncrosslinked and polyol-crosslinked polyacrylic acids, acrylamidopropyltrimethylammonium chloride/acrylate copolymers, octylacrylamide/methyl methacrylate/tert. butylaminoethyl methacrylate/2-hydroxypropyl methacrylate copolymers, polyvinylpyrrolidone, vinylpyrrolidone/vinyl acetate copolymers, vinylpyrrolidone/dimethylaminoethyl methacrylate/vinyl caprolactam terpolymers and optionally derivatized cellulose ether and silicones.

Silicone Compounds

Examples of suitable silicone compounds are dimethylpolysiloxanes, methylphenylpolysiloxanes, cyclic silicones together with amino-, fatty acid-, alcohol-, polyether-, epoxy-, fluorine-, glycoside- and/or alkyl-modified silicone compounds, which may assume both liquid and resin form at room temperature. Also suitable are simethicones, which comprise mixtures of dimethicones with an average chain length of 200 to 300 dimethylsiloxane units and hydrogenated silicates.

UV Light Protection Filters and Antioxidants

Polyethylene glycol esters of the formula 1 and in particular the preparations according to the invention containing at least one polyethylene glycol ester of the formula 1 and at least one polyethylene glycol ether of the formula 2 may also promote the solubility behavior of light protection filters and antioxidants in cosmetic and dermatological preparations.

Typical examples of corresponding sun protection factors are

UV-B filters such as for example:
p-aminobenzoic acid
p-aminobenzoic acid ethyl ester (25 mol), ethoxylated
p-dimethylaminobenzoic acid 2-ethylhexyl ester
p-aminobenzoic acid ethyl ester (2 mol), N-propoxylated
p-aminobenzoic acid glycerol ester
salicylic acid homomethyl ester (Homosalate) (Neo Heliopan®HMS)
salicylic acid 2-ethylhexyl ester (Neo Heliopan®OS)
triethanolamine salicylate
4-isopropylbenzyl salicylate
anthranilic acid menthyl ester (Neo Heliopan®MA)
diisopropylcinnamic acid ethyl ester
p-methoxycinnamic acid 2-ethylhexyl ester (Neo Heliopan®AV)
diisopropylcinnamic acid methyl ester
p-methoxycinnamic acid isoamyl ester (Neo Heliopan®E 1000)
p-methoxycinnamic acid diethanolamine salt
p-methoxycinnamic acid isopropyl ester
2-phenylbenzimidazolsulfonic acid and salts (Neo Heliopan®Hydro)
3-(4'-trimethylammonium)-benzylidene-bornan-2-one methyl sulfate
β-imidazole-4(5)-acrylicacid (urocaninic acid)
3-(4'-sulfo)benzylidene-bornan-2-one and salts
3-(4'-methylbenzylidene)-d,l-camphor (Neo Heliopan®MBC)
3-benzylidene-d,l-camphor
N-[(2 and 4)-[2-(oxoborn-3-ylidene)methyl]benzyl]acrylamide polymer
4,4'-[(6-[4-(1,1-dimethyl)-aminocarbonyl)-phenylamino]-1,3,5-triazine-2,4-diyl)diimino]-bis-(benzoic acid 2-ethylhexyl ester) (Uvasorb®HEB)
benzylidene malonate/polysiloxane (Parsol®SLX)
glyceryl ethyl hexanoate dimethoxycinnamate
dipropylene glycol salicylate
tris(2-ethylhexyl)-4,4',4''-(1,3,5-triazine-2,4,6-triyltriimino) tribenzoate (Uvinul®T150)

Broadband filters such as for example:
2-ethylhexyl-2-cyano-3,3-diphenyl acrylate (Neo Heliopan®303)
ethyl-2-cyano-3,3'-diphenyl acrylate
2-hydroxy-4-methoxybenzophenone 5-sulfonic acid
sodium hydroxymethoxybenzophenone sulfonate
disodium 2,2'-dihydroxy-4,4'-dimethoxy-5,5'-disulfobenzophenone
phenol, -(2H-benzotriazol-2-yl)-4-methyl-6-(2-methyl-3(1,3,3,3-tetramethyl-1-(trimethylsilyl)-oxy)-disiloxanyl)-propyl), (Mexoryl®XL)
2,2'-methylene-bis-(6-(2H-benzotriazol-2-yl)-4-1,1,3,3-tetramethylbutyl)phenol), (Tinosorb®M)
2,4-bis-[4-(2-ethylhexyl)-2-hydroxyphenyl]-1,3,5-triazine
2,4-bis-[{(4-(2-ethyl-hexyloxy)-2-hydroxy}-phenyl]-6-(4-methoxyphenyl)-1,3,5-triazine, (Tinosorb®S)
2,4-bis-[{(4-(3-sulfonato)-2-hydroxy-propyloxy)-2-hydroxy}-phenyl]-6-(4-methoxyphenyl)-1,3,5-triazine sodium salt
2,4-bis-[{(3-(2-propyloxy)-2-hydroxy-propyloxy)-2-hydroxy}-phenyl]-6-(4-methoxyphenyl)-1,3,5-triazine
2,4-bis-[{4-(2-ethyl-hexyloxy)-2-hydroxy}-phenyl]-6-[4-(2-methoxyethylcarbonyl)-phenylamino]-1,3,5-triazine
2,4-bis-[{4-(3-(2-propyloxy)-2-hydroxy-propyloxy)-2-hydroxy}-phenyl]-6-[4-(2-ethylcarboxyl)-phenylamino]-1,3,5-triazine
2,4-bis-[{4-(2-ethyl-hexyloxy)-2-hydroxy}-phenyl]-6-(1-methyl-pyrrol-2-yl)-1,3,5-triazine
2,4-bis-[{4-tris-(trimethylsiloxy-silylpropyloxy)-2-hydroxy}-phenyl]-6-(4-methoxyphenyl)-1,3,5-triazine
2,4-bis-[{4-(2''-methylpropenyloxy)-2-hydroxy}-phenyl]-6-(4-methoxyphenyl)-1,3,5-triazine
2,4-bis-[{4-(1',1',1',3',5',5',5'-heptamethylsiloxy-2''-methyl-propyloxy)-2-hydroxy}-phenyl]-6-(4-methoxyphenyl)-1,3,5-triazine UV-A filters such as for example:
terephthalylidene-dibornanesulfonic acid and salts (Mexoryl®SX)
4-t-butyl-4'-methoxy-dibenzoylmethane (Avobenzon)/(Neo Heliopan®357)
phenylene-bis-benzimidazyl-tetrasulfonic acid disodium salt (Neo Heliopan®AP)
2,2'-(1,4-phenylene)-bis-(1H-benzimidazole-4,6-disulfonic acid), monosodium salt
2-(4-diethylamino-2-hydroxybenzoyl)-benzoic acid hexylester (Uvinul® A Plus)
4-isopropyldibenzoylmethane
indanylidene compounds according to DE 100 55 940 (=WO 02/38537)

UV absorbers particularly suitable for combining are:
p-aminobenzoic acid
3-(4'-trimethylammonium)-benzylidene-bornan-2-one methyl sulfate
salicylic acid homomethyl ester (Neo Heliopan®HMS)
2-phenylbenzimidazolsulfonic acid (Neo Heliopan®Hydro)
terephthalylidene-dibornanesulfonic acid and salts (Mexoryl®SX)
4-tert.-butyl-4'-methoxydibenzoylmethane (Neo Heliopan®357)
3-(4'-sulfo)benzylidene-bornan-2-one and salts
2-ethylhexyl-2-cyano-3,3-diphenyl acrylate (Neo Heliopan®303)
N-[(2 and 4)-[2-(oxoborn-3-ylidene)methyl]benzyl]acrylamide polymer
p-methoxycinnamic acid 2-ethylhexyl ester (Neo Heliopan®AV)
p-aminobenzoic acid ethyl ester (25 mol), ethoxylated
p-methoxycinnamic acid isoamyl ester (Neo Heliopan®E1000)
2,4,6-trianilino-(p-carbo-2'-ethylhexyl-1'-oxy)-1,3,5-triazine (Uvinul®T150)
phenol, 2-(2H-benzotriazol-2-yl)-4-methyl-6-(2-methyl-3 (1,3,3,3-tetramethyl-1-(trimethylsilyl)-oxy)-disiloxanyl)-propyl), (Mexoryl®XL)
4,4'-[(6-[4-(1,1-dimethyl)-aminocarbonyl)-phenylamino]-1,3,5-triazine-2,4-diyl)diimino]-bis-(benzoic acid 2-ethylhexyl ester) (Uvasorb HEB)
3-(4'-methylbenzylidene)-d,l-camphor (Neo Heliopan®MBC)
3-benzylidenecamphor
salicylic acid 2-ethylhexyl ester (Neo Heliopan®OS)

4-dimethylaminobenzoic acid 2-ethylhexyl ester (Padimate O)

hydroxy-4-methoxy-benzophenone 5-sulfonic acid and Na salt 2,2'-methylene-bis-(6-(2H-benzotriazol-2-yl)-4-1,1,3,3-tetramethylbutyl)-phenol), (Tinosorb®M)

phenylene-bis-benzimidazyl-tetrasulfonic acid disodium salt (Neo Heliopan®AP)

2,4-bis-[{(4-(2-ethyl-hexyloxy)-2-hydroxy}-phenyl]-6-(4-methoxyphenyl)-1,3,5-triazine, (Tinosorb®S)

benzylidene malonate/polysiloxane (Parsol®SLX)

menthylanthranilate (Neo Heliopan®MA)

2-(4-diethylamino-2-hydroxybenzoyl)-benzoic acid hexylester (Uvinul® A Plus)

indanylidene compounds according to DE 100 55 940 (=WO 02/38537)

It is also possible to use in preparations according to the invention particulate UV filters or inorganic pigments which may optionally be hydrophobized, such as the oxides of titanium ($TiO_2$), zinc (ZnO), iron ($Fe_2O_3$), zirconium ($ZrO_2$), silicon ($SiO_2$), manganese (for example MnO), aluminum ($Al_2O_3$), cerium (for example $Ce_2O_3$) and/or mixtures.

In addition to the above-stated light protection substances, the solubility behavior of antioxidants in cosmetic and dermatological preparations may also be promoted by the polyethylene glycol esters of the formula 1 and in particular by the preparations according to the invention containing at least one polyethylene glycol ester of the formula 1 and at least one polyethylene glycol ether of the formula 2. Typical examples of antioxidants are amino acids (for example glycine, histidine, tyrosine, tryptophan) and the derivatives thereof, imidazoles (for example urocaninic acid) and the derivatives thereof, peptides such as D,L-carnosine, D-carnosine, L-carnosine and the derivatives thereof (for example Anserin), carotenoids, carotenes (for example alpha-carotene, beta-carotene, lycopene) and the derivatives thereof, chlorogenic acid and the derivatives thereof, lipoic acid and the derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, gamma-linoleyl, cholesteryl and glyceryl esters thereof) and the salts thereof, dilauryl thiodipropionate, distearyl thiodipropionate, thiodipropionic acid and the derivatives thereof (esters, ethers, peptides, lipids, nucleotides, nucleosides and salts) and sulfoximine compounds (for example buthionine sulfoximines, homocysteine sulfoximine, buthionine sulfones, penta-, hexa-, heptathionine sulfoximine) in very small compatible rates of addition (for example pmol to mu mol/kg), also (metal) chelating agents (for example alpha-hydroxyfatty acids, palmitic acid, phytic acid, lactoferrin), alpha-hydroxy acids (for example citric acid, lactic acid, malic acid), humic acid, bile acid, bile extracts, bilirubin, biliverdin, EDTA, EGTA and the derivatives thereof, unsaturated fatty acids and the derivatives thereof (for example gamma-linolenic acid, linoleic acid, oleic acid), folic acid and the derivatives thereof, ubiquinone and ubiquinol and the derivatives thereof, vitamin C and derivatives (for example ascorbyl palmitate, Mg ascorbyl phosphate, ascorbyl acetate), tocopherols and derivatives (for example vitamin E acetate), vitamin A and derivatives (vitamin A palmitate) as well as coniferyl benzoate of benzoic resin, rutinic acid and the derivatives thereof, alpha-glycosyl rutin, ferulic acid, furfurylidene glucitol, carnosine, butylhydroxytoluene, butylhydroxyanisole, nordihydroguaiac resin acid, nordihydroguaiaretic acid, trihydroxybutyrophenone, uric acid and the derivatives thereof, mannose and the derivatives thereof, superoxide dismutase, zinc and the derivatives thereof (for example ZnO, ZnSO4) selenium and the derivatives thereof (for example selenium methionine), stilbenes and the derivatives thereof (for example stilbene oxide, trans-stilbene oxide) and derivatives suitable according to the invention (salts, esters, ethers, sugars, nucleotides, nucleosides, peptides and lipids) of these stated active ingredients.

Antiirritants and Pruritus-Relieving Active Ingredients

Polyethylene glycol esters according to the invention of the formula 1 and in particular the preparations according to the invention containing at least one polyethylene glycol ester of the formula 1 and at least one polyethylene glycol ether of the formula 2 may also promote the solubility behavior of antiirritants and pruritus-relieving active ingredients in cosmetic and dermatological preparations. Antiinflammatory or erythema- and/or pruritus-relieving active ingredients suitable or commonly used for cosmetic and/or dermatological applications are steroidal antiinflammatory substances of the corticosteroid type such as for example hydrocortisone or hydrocortisone derivatives such as for example hydrocortisone 17-butyrate, dexamethasone, dexamethasone phosphate, methylprednisolone or cortisone, wherein the list may be extended by the addition of further steroidal antiinflammatory drugs. Nonsteroidal antiinflammatory drugs are for example oxicams such as piroxicam or tenoxicam; salicylates such as aspirin, Disalcid, Solprin or Fendosal; acetic acid derivatives such as diclofenac, fenclofenac, indomethacin, sulindac, tolmetin, or clindanac; fenamates such as mefenamic, meclofenamic, flufenamic or niflumic; propionic acid derivatives such as ibuprofen, naproxen, benoxaprofen or pyrazoles such as phenylbutazone, oxyphenylbutazone, febrazone or azapropazone. Natural antiinflammatory or erythema- and/or pruritus-relieving substances are for example also plant extracts, specifically highly active plant extract fractions and high purity active substances isolated from plant extracts. Particular preference is given to extracts, fractions and active substances from chamomile, ginger, aloe vera, Commiphora species, Rubia species, willows, willowherb, oats, calendula, arnica, St. John's wort, honeysuckle, rosemary, Passiflora incarnata, witch hazel, ginger, echinacea or oats, together with pure substances such as inter alia (alpha-)bisabolol, gingerols, shogaols, apigenin, apigenin-7-glucoside, boswellia acid, phytosterols, glycyrrhizinic acid, glabridin, licochalcone A and anthranilic acid amides of natural or indeed synthetic origin in particular from the groups of avenanthramides and dianthramides. Further pruritus-relieving active ingredients are for example polydocanol (laureth-9), doxepin hydrochlorides, mepyramine, diphenhydramine, clorphenamine, cetirizine, diazepam, cimetidine, bamipine lactate, benzocaine, lidocaine (lignocaine), ondansetrone, paroxetine, mirtazapine, chlorcyclizine hydrochlorides, levomepromazine, diazepam, tranilast, salicylic acid and esters of salicylic acid, pimecrolimus, capsaicin, nalbuphine, pramoxine, zinc oxide, zinc acetate, strontium nitrate, phenol and camphor. Further pruritus-relieving active ingredients are for example opioid receptor antagonists and agonists such as inter alia p opioid receptor antagonists (β-endorphin antagonists) such as naltrexone, naloxone, nalmefene, morphine, codeine or bupreorphine and K-opioid receptor agonists (dynorphin A agonists) such as for example TRK-820, U50448H, nor-binaltorphimine or pentazocine. Further pruritus-relieving active ingredients are for example cannabinoid receptor agonists such as anandamide, 2-arachidonylglycerol, N-palmitoylethanolamine, N-acetylethanolamine, oleamide or HU210. Further pruritus-relieving active ingredients are, moreover, androgens such as for example norethandrolone, methyltestosterone, stanozolol, danazol, fluoxymesterone or oxandrolone. Further pruritus-relieving active ingredients are rifampicin, phenobarbital, colestyramine, or thalidomide and PAR-2 receptor antagonists.

Antiaging Active Ingredients

Polyethylene glycol esters according to the invention of the formula 1 and in particular the preparations according to the invention containing at least one polyethylene glycol ester of the formula 1 and at least one polyethylene glycol ether of the formula 2 may also promote the solubility behavior of antiaging active ingredients in cosmetic and dermatological preparations. Advantageous active ingredients against skin aging and wrinkling are in this respect soy protein or protein hydrolysates, soy isoflavones, hydrolyzed rice protein, hydrolyzed hazelnut protein, oligopeptides from hydrolyzed Hibiscus esculentus extract, wheat protein, 3-glucans for example from oats and the derivatives thereof, glycoproteins, ursolic acid and the salts thereof, betulin, betulinic acid and the salts thereof, retinol, retinol palmitate, propyl gallate, precocenes, 6-hydroxy-7-methoxy-2,2-dimethyl-1(2H)-benzopyran, 3,4-dihydro-6-hydroxy-7-methoxy-2,2-dimethyl-1 (2H)-benzopyran, creatine or other synthetic or natural active ingredients against skin aging and wrinkling, wherein the latter may also be used in the form of an extract from plants, such as for example green tea, *Rubus fruticosus, Sanguisorba officinalis, Centella asiatica, Ribes nigrum, Passiflora incarnata, Filipendula ulmaria, Phyllanthus emblica, Potentilla* species, okra, algae, evening primrose, pomegranate, lady's mantle rosemary, sage, echinacea, birch, apple or soy. Particularly preferred for use as further active ingredients against skin aging are 3-glucans, with 1,3-1,4-linked 3-glucan from oats, *Rubus* fruticosus extract or wheat protein.

Cooling Active Ingredients

Polyethylene glycol esters of the formula 1 and in particular the preparations according to the invention containing at least one polyethylene glycol ester (preferably according to the invention) of the formula 1 and at least one polyethylene glycol ether of the formula 2 may also promote the solubility behavior of cooling active ingredients in cosmetic and dermatological preparations.

Cooling active ingredients are: l-menthol, d-menthol, racemic menthol, menthone glycerol acetal (trade name: Frescolat®MGA), menthyl lactate (trade name: Frescolat®ML, the menthyl lactate preferably comprising l-menthyl lactate, in particular l-menthyl l-lactate), substituted menthyl 3-carboxamides (for example menthyl 3-carboxylic acid N-ethylamide), 2-isopropyl-N-2,3-trimethylbutanamide, substituted cyclohexane carboxamides, 3-menthoxypropane-1,2-diol, 2-hydroxyethylmenthyl carbonate, 2-hydroxypropylmenthyl carbonate, N-acetyl glycine menthyl ester, isopulegol, menthylhydroxycarboxylic acid ester (for example menthyl 3-hydroxybutyrate), monomenthyl succinate, 2-mercaptocyclodecanone, menthyl 2-pyrrolidin-5-one carboxylate, 2,3-dihydroxy-p-menthane, 3,3,5-trimethylcyclohexanone glycerol ketal, 3-menthyl 3,6-di- and -trioxaalkanoates, 3-menthyl methoxyacetate, icilin.

Preferred cooling active ingredients are: l-menthol, d-menthol, racemic menthol, menthone glycerol acetal (trade name: Frescolat®MGA), menthyl lactate (preferably l-menthyl lactate, in particular l-menthyl l-lactate, trade name: Frescolat®ML), substituted menthyl 3-carboxamides (for example menthyl 3-carboxylic acid N-ethylamide), 2-isopropyl-N-2,3-trimethylbutanamide, substituted cyclohexanoic carboxamides, 3-menthoxypropane-1,2-diol, 2-hydroxyethylmenthyl carbonate, 2-hydroxypropylmenthyl carbonate, isopulegol.

Particularly preferred cooling active ingredients are: l-menthol, racemic menthol, menthone glycerol acetal (trade name: Frescolat®MGA), menthyl lactate (preferably l-menthyl lactate, in particular l-menthyl l-lactate, trade name: Frescolat®ML), 3-menthoxypropane-1,2-diol, 2-hydroxyethylmenthyl carbonate, 2-hydroxypropylmenthyl carbonate.

Very particularly preferred cooling active ingredients are: l-menthol, menthone glycerol acetal (trade name: Frescolat®MGA), menthyl lactate (preferably l-menthyl lactate, in particular l-menthyl l-lactate, trade name: Frescolat®ML).

The usage concentration of the cooling active ingredients to be used lies, depending on the substance, preferably in the concentration range of from 0.01 to wt. % and preferably in the concentration range of from 0.1 to 5 wt. %, relative to the total mass of the finished (ready-to-use), preferably cosmetic or dermatological preparation.

Skin Moisture Regulators

Polyethylene glycol esters of the formula 1 and in particular the preparations according to the invention containing at least one polyethylene glycol ester of the formula 1 and at least one polyethylene glycol ether of the formula 2 may also promote the solubility behavior of skin moisture regulators in cosmetic and dermatological preparations. The following substances are examples of substances used as moisture-retaining regulators ("moisturizers"): sodium lactate, urea and urea derivatives, alcohols, glycerol, diols such as propylene glycol, 1,2-pentanediol, 1,2-hexanediol, 1,2-octanediol and 1,2-decanediol, collagen, elastin or hyaluronic acid, diacyladipates, petroleum jelly, urocaninic acid, lecithin, panthenol, phytantriol, lycopin, (pseudo-)ceramides, glycosphingolipids, cholesterol, phytosterols, chitosan, chondroitin sulfate, lanolin, lanolin esters, amino acids, alpha-hydroxy acids, (for example citric acid, lactic acid, malic acid) and the derivatives thereof, mono-, di- and oligosaccharides such as for example glucose, galactose, fructose, mannose, fruit sugar and lactose, polysugars such as 3-glucans, in particular 1,3-1,4-β-glucan from oats, alpha-hydroxyfatty acids, triterpene acids such as betulinic acid or ursolic acid, algae extracts.

Osmolytes

Polyethylene glycol esters of the formula 1 and in particular the preparations according to the invention containing at least one polyethylene glycol ester (preferably according to the invention) of the formula 1 and at least one polyethylene glycol ether of the formula 2 may also promote the solubility behavior of osmolytes in cosmetic and dermatological preparations. Example of osmolytes which may be stated are: substances from the group comprising sugar alcohols (myo-inositol, mannitol, sorbitol), quaternary amines such as taurine, choline, betaine, betaine/glycine, ectoin, diglycerol phosphate, phosphorylcholine, glycerophosphorylcholine, amino acids such as glutamine, glycine, alanine, glutamate, aspartate or proline, phosphatidyl choline, phosphatidyl inositol, inorganic phosphates, and polymers of the stated compounds such as proteins, peptides, polyamino acids and polyols. All osmolytes simultaneously have a skinmoisturizing effect.

Plant Extracts

Polyethylene glycol esters of the formula 1 and in particular the preparations according to the invention containing at least one polyethylene glycol ester (preferably according to the invention) of the formula 1 and at least one polyethylene glycol ether of the formula 2 may also promote the solubility behavior of plant extracts in cosmetic and dermatological preparations. With regard to the plant extracts which may be used, reference is made in particular to the extracts which are listed in the table starting on page 44 of the 3rd edition of the "Leitfaden zur Inhaltsstoffdeklaration kosmetischer Mittel" ["Guidelines for the nomenclature of ingredients in cosmetic agents"], published by the German Cosmetic, Toiletry, Perfumery and Detergent Association (IKW), Frankfurt. The following are in particular advantageous: extracts from aloe, witch hazel, algae, oak bark, willowherb, stinging nettle, dead nettle, hops, chamomile, yarrow, arnica, *calendula*, burdock root, horsetail, hawthorn, lime blossom, almond, pine-needle, horse chestnut, sandalwood, juniper, coconut, mango, apricot, orange, lemon, lime, grapefruit, apple, green tea, grapefruit seed, wheat, oats, barley, sage, thyme, wild thyme, rosemary, birch, mallow, lady's smock, willow bark, restharrow, coltsfoot, marsh mallow, ginseng and ginger root.

Particular preference is given to extracts from aloe vera, chamomile, algae, rosemary, *calendula*, ginseng, cucumber, sage, stinging nettle, lime blossom, arnica, and witch hazel. Mixtures of two or more plant extracts may also be used. Extracting agents for producing the stated plant extracts include water, alcohols and mixtures thereof.

Skin-Lightening Substances

Polyethylene glycol esters of the formula 1 and in particular the preparations according to the invention containing at least one polyethylene glycol ester (preferably according to the invention) of the formula 1 and at least one polyethylene glycol ether of the formula 2 may also promote the solubility behavior of skinlightening substances in cosmetic and dermatological preparations. Advantageous skin-lightening active ingredients are in this respect kojic acid (5-hydroxy-2-hydroxymethyl-4-pyranone), kojic acid derivatives such as for example kojic acid palmitate, arbutin, ascorbic acid, ascorbic acid derivatives, hydroquinone, hydroquinone derivatives, resorcinol, sulfur-containing molecules such as for example glutathione, or cysteine, alpha-hydroxy acids, (for example citric acid, lactic acid, malic acid) and the derivatives thereof, N-acetyl tyrosine and derivatives, undecenoyl phenylalanine, gluconic acid, 4-alkylresorcinols, diphenylmethane derivatives such as for example 4-(1-phenylethyl)1,3-benzenediol, chromone derivatives such as aloesin, flavonoids, thymol derivatives, 1-aminoethylphosphinic acid, thiourea derivatives, ellagic acid, nicotinamide, zinc salts such as for example zinc chloride or gluconate, thujaplicin and derivatives, triterpenes such as maslinic acid, sterols such as ergosterol, benzofuranones such as senkyunolide, vinyl and ethyl guaiacol, dione acids such as octodecene dione acid and azelaic acid, inhibitors of nitrogen oxide synthesis such as for example, L-nitroarginine and the derivatives thereof, 2,7-dinitroindazole or thiocitrulline, metal chelators (for example alpha-hydroxyfatty acids, palmitic acid, phytic acid, lactoferrin, humic acid, bile acid, bile extracts, bilirubin, biliverdin, retinoids, soy milk, soy extract, serine protease inhibitors or lipoic acid or other synthetic or natural active ingredients for lightening skin and hair, wherein the latter may also be used in the form of an extract from plants, such as for example bearberry extract, rice extract, papaya extract, liquorice root extract or concentrated constituents thereof such as glabridin, or licochalcone A, *Artocarpus* extract, extract of *Rumex* and *Ramulus* species, extracts from pine species (Pinus) and extracts from *Vitis* species or stilbene derivatives concentrated therefrom, extract of saxifrage, mulberry, skullcap and/or grapes.

Skin-Tanning Active Ingredients

Polyethylene glycol esters of the formula 1 and in particular the preparations according to the invention containing at least one polyethylene glycol ester, preferably according to the invention, of the formula 1 and at least one polyethylene glycol ether of the formula 2 may also promote the solubility behavior of skin-tanning substances in cosmetic and dermatological preparations. Advantageous skin-lightening active ingredients are substrates or substrate analogs of tyrosinase such as L-tyrosine, L-DOPA or L-dihydroxyphenylalanine, stimulators of tyrosinase activity or expression such as theophylline, caffeine, proopiomelanocortin peptides such as ACTH, alpha-MSH, the peptide analogs thereof and other substances which bind to the melanocortin receptor, peptides such as ValGly-Val-Ala-Pro-Gly, Lys-Ile-Gly-Arg-Lys or Leu-Ile-Gly-Lys, purines, pyrimidines, folic acid, copper salts such as copper gluconate, chloride or pyrrolidonate, flavonoids, flavanone glycosides such as naringin and hesperidin, melanin derivatives such as Melasyn-100 and MelanZe, diacylglycerols, aliphatic or cyclic diols, psoralens, prostaglandins and the analogs thereof, activators of adenylate cyclase and compounds which activate the transfer of melanosomes in keratinocytes such as serine proteases or PAR-2 receptor agonists, extracts from plants and plant parts of the Chrysanthemum species, Sanguisorba species, walnut extracts, urucum extracts, rhubarb extracts, erythrulose and dihydroxyacetone.

Antimicrobial Active Ingredients

Polyethylene glycol esters of the formula 1 and in particular the preparations according to the invention containing at least one polyethylene glycol ester (preferably according to the invention) of the formula 1 and at least one polyethylene glycol ether of the formula 2 may also promote the solubility behavior of substances which are used primarily to inhibit the growth of undesired microorganisms or in animal organisms in cosmetic and dermatological preparations. Advantageous antimicrobial active ingredients are in this respect, in addition to the large group of classical antibiotics, in particular products relevant for cosmetics such as triclosan, climbazole, zinc pyrithione, ichthyol, Octopirox (1-hydroxy-4-methyl-6-(2,4,4-trimethylpentyl)-2(1H)-pyridone, 2-aminoethanol), chitosan, farnesol, octoxyglycerol, glycerol monolaurate, arylalkyl alcohols such as for example phenylethyl alcohol, 3-phenyl-1-propanol, veticol or muguet alcohol, polyglycerol esters such as for example polyglycerol-3 caprylates and aliphatic diols such as for example 1,2-decanediol or combinations of the stated substances, which are used inter alia against armpit odor, foot odor or dandruff.

Antidandruff Agents

Polyethylene glycol esters of the formula 1 and in particular the preparations according to the invention containing at least one polyethylene glycol ester (preferably according to the invention) of the formula 1 and at least one polyethylene glycol ether of the formula 2 may also improve the solubility behavior of antidandruff agents. Antidandruff agents are here preferably selected from the azole group consisting of climbazole, benzimidazole, benzothiazole, bifonazole, butaconazole nitrate, clotrimazole, croconazole, eberconazole, econazole, elubiol, fenticonazole, fluconazole, flutimazole, isoconazole, ketoconazole, lanoconazole, metronidazole, miconazole, neticonazole, omoconazole, oxiconazole nitrate, sertaconazole, sulconazole nitrate, thioconazole and diazoles and triazoles, preferably terconazole and itraconazole and any desired combinations of the stated azoles. Alternatively or in addition to the azoles, pyrithione salts, preferably-hydroxy-2-pyrithione salts, may be used as antidandruff agents. Pyrithione salts which are preferred in this respect are the metal cations of sodium, zinc, tin, cadmium, magnesium, aluminum and zirconium. Particular preference is given to the zinc salt of 1-hydroxy-2-pyrithione (known as "zinc pyrithione" or "ZPT"). Alternatively or in addition to the azoles and/or pyrithione salts, further antidandruff agents may also preferably be selected from the group consisting of coal tar; sulfur; selenium disulfide; aluminum chloride; Octopirox (INCI: Piroctone Olamine); cyclopiroxolamine; undecenoic acid and the metal salts thereof; potassium permanganate; sodium thiosulfate, urea preparations, griseofulvin, 8-hydroxyquinoline, clioquinol, thiobendazole; thiocarbamates; triclosan; haloprogin; polyenes; hydroxypyridone; morpholine; benzylamine; allylamine, preferably terbinafine; tea tree oil; clove leaf oil; coriander oil; palmarosa oil; thyme oil; cinnamon oil and essential oil of bitter orange; cinnamaldehyde; citronellic acid; farnesol; berberine; hinokitiol; tropolone; birch tar oil; ichthyol (sulfonated slate flour) Sensiva SC-50 (ethylhexyl glycerol); polyglycerol esters, preferably polyglycerol 3-caprylate; arylalkyl alcohols, preferably phenylethyl alcohol; 3-phenyl-1-propanol; veticol, (4-methyl-4-phenyl-2-pentanol); muguet alcohol 2,2-dimethyl-3-phenylpropanol; Elestab HP-100; azelaic acid; lyticase; isothiazolinones, preferably octyl isothiazolinone and iodopropynylbutyl carbamate and 1,2-decanediol, 1,2-dodecanediol and 1,2-tetradecanediol.

Antiacne Active Ingredients

Polyethylene glycol esters of the formula 1 and in particular the preparations according to the invention containing at least one polyethylene glycol ester (preferably according to the invention) of the formula 1 and at least one polyethylene glycol ether of the formula 2 may also improve the solubility behavior of antiacne active ingredients selected from the group consisting of benzoyl peroxide, azelaic acid, salicylic acid, retinoids, such as all-trans-retinoic acid (tretinoin), all-trans-retinal or cis-13-retinoic acid (isotretinoin) and of antibiotics which are used specifically to treat acne, such as for example clindamycin, erythromycin, tetracycline, doxycycline and/or sulfur, also chlorhexidine, triclosan, bisabolol, farnesol and phenoxyethanol as well as isoflavonoids (e.g. genistein, daidzein, genistin and glycitein).

Antiperspirants

Polyethylene glycol esters of the formula 1 and in particular the preparations according to the invention containing at least one polyethylene glycol ester (preferably according to the invention) of the formula 1 and at least one polyethylene glycol ether of the formula 2 may also promote the solubility behavior of antiperspirant substances in cosmetic and dermatological preparations. Antiperspirant active ingredients primarily include all aluminum salts such as aluminum chloride, aluminum hydrochloride, nitrate, sulfate, acetate etc. In addition, however, the use of zinc, magnesium and zirconium compounds may also be advantageous. For use in cosmetic and dermatological antiperspirants, the aluminum salts and, to a somewhat lesser degree, aluminum/zirconium salt combinations have proven effective. Also worthy of mention are the partially neutralized and thus more skin compatible, but not quite so active aluminum hydroxychlorides. In addition to aluminum salts, further substances are also feasible, such as for example a) protein-precipitating substances such as inter alia formaldehyde, glutaraldehyde, natural and synthetic tannins together with trichloroacetic acid, which bring about superficial closure of the sweat glands, b) local anesthetics (inter alia diluted solutions of for example lidocaine, prilocalne or mixtures of such substances), which switch off sympathetic supply of the sweat glands by blockading the peripheral nerve pathways, c) zeolites of the X-, A- or Y-type, which, in addition to reducing sweat secretion, also function as adsorbents for bad odors and d) botulinum toxin (toxin of the bacterium *Clostridium botulinum*), which is also used in the case of hyperhydrosis, i.e. pathologically elevated sweat secretion, and whose action is based on irreversible blocking of the release of the transmitter substance acetylcholine which is of relevance in sweat secretion.

Enzyme Inhibitors

Polyethylene glycol esters of the formula 1 and in particular the preparations according to the invention containing at least one polyethylene glycol ester (preferably according to the invention) of the formula 1 and at least one polyethylene glycol ether of the formula 2 may also promote the solubility behavior of enzyme inhibitors in cosmetic and dermatological preparations. Examples of suitable enzyme inhibitors are esterase inhibitors. These preferably comprise trialkyl citrates such as trimethyl citrate, tripropyl citrate, triisopropyl citrate, tributyl citrate and in particular triethyl citrate (Hydagen™ CAT). These substances inhibit enzyme activity and so reduce odor formation. Further substances which are feasible as esterase inhibitors are sterol sulfates or phosphates, such as for example lanosterol, cholesterol, campesterol, stigmasterol and sitosterol sulfate or phosphate, dicarboxylic acids and the esters thereof, such as for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and the esters thereof such as for example citric acid, malic acid, tartaric acid or tartaric acid diethyl ester, and zinc glycinate.

Odor Absorbers

Polyethylene glycol esters of the formula 1 and in particular the preparations according to the invention containing at least one polyethylene glycol ester (preferably according to the invention) of the formula 1 and at least one polyethylene glycol ether of the formula 2 may also promote the solubility behavior of odor absorbers in cosmetic and dermatological preparations. Suitable as odor absorbers are substances which may absorb and largely retain odor-forming compounds. They lower the partial pressure of the individual components and thus also reduce their speed of propagation. It is important that perfumes remain unaffected thereby. Odor absorbers are not effective against bacteria. They contain as their main constituent, for example, a complex zinc salt of ricinoleic acid or specific, largely odor-neutral fragrances, which are known to a person skilled in the art as "fixatives", such as for example extracts of labdanum oil or *styrax* oil or certain abietic acid derivatives.

Insect Repellents

Polyethylene glycol esters of the formula 1 and in particular the preparations according to the invention containing at least one polyethylene glycol ester (preferably according to the invention) of the formula 1 and at least one polyethylene glycol ether of the formula 2 may also promote the solubility behavior of insect repellents in cosmetic and dermatological preparations. Insect repellents are for example IR 3225, citrus oils, eucalyptus oil, N,N-diethyltoluamide (DEET), dibutyl phthalate, dimethyl phthalate, indalone, 2-ethyl-1,3-hexanediol, menthone glycerol acetal, menthyl lactate, menthyl 2-hydroxypropyl carbonate, N-substituted p-menthane carboxamides such as N-ethyl-p-menthane-3-carboxamide, p-menthane-3,8-diol, isopulegol, citronellol, citronellal-p-menthane-3,8-diol acetal, menthyl pyrrolidone carboxylate. Further common repellents may be found in "W. Raab and U. Kindl, "Pflegekosmetik" ["Care cosmetics"], Gustav-Fischer-Verlag Stuttgart/New York, 1991, p. 161. The repellents may be incorporated alone into the preparation or in combination with other substances or active ingredients.

Preservatives

Polyethylene glycol esters of the formula 1 and in particular the preparations according to the invention containing at least one polyethylene glycol ester (preferably according to the invention) of the formula 1 and at least one polyethylene glycol ether of the formula 2 may also promote the solubility behavior of preservatives in cosmetic and dermatological preparations. Common preservatives which are used are benzoic acid, the esters and salts thereof, propionic acid and the salts thereof, salicylic acid and the salts thereof, 2,4-hexadienoic acid (sorbic acid) and the salts thereof, formaldehyde and paraformaldehyde, 2-hydroxybiphenyl ether and the salts thereof, 2-zinc sulfidopyridine N-oxide, inorganic sulfites and bisulfites, sodium iodate, chlorobutanol, 4-ethylmercury (II) 5-amino-1,3-bis(2-hydroxybenzoic acid), the salts and esters thereof, dehydracetic acid, formic acid, 1,6-bis(4-amidino-2-bromophenoxy)-n-hexane and the salts thereof, the sodium salt of ethylmercury(II) thiosalicylic acid, phenylmercury and the salts thereof, 10-undecenoic acid and the salts thereof, 5-amino-1,3-bis(2-ethylhexyl)-5-methyl-hexahydropyrimidine, 5-bromo-5-nitro-1,3-dioxane, 2-bromo-2-nitro-1,3-propanediol, 2,4-dichlorobenzyl alcohol, N-(4-chlorophenyl)N'-(3,4-dichlorophenyl)-urea, 4-chloro-m-cresol, 2,4,4'-trichloro-2'-hydroxydiphenyl ether, 4-chloro-3,5-dimethylphenol, 1,1'-methylene-bis(3-(1-hydroxymethyl-2,4-dioximidazolidin-5-yl)urea), poly(hexamethylene biguanide) hydrochloride, 2-phenoxyethanol, hexamethylene tetramine, 1-(3-chloroallyl)-3,5,7-triaza-1-azonia adamantane chloride, 1-(4-chlorophenoxy)1 (1H-imidazol-1-yl)-3,3-dimethyl-2-butanone, 1,3-bis-(hydroxymethyl)-5,5-dimethyl-2,4-imidazolidinedione, benzyl alcohol, Octopirox, 1,2-dibromo-2,4-dicyanobutane, 2,2'-methylene-bis(6-bromo-4-chlorophenol), bromochlorophene, mixture of 5-chloro-2-methyl-3(2H)-isothiazolinone and 2-methyl-3(2H) isothiazolinone with magnesium chloride and magnesium nitrate, 2-benzyl-4-chlorophenol, 2-chloroacetamide, chlorhexidine, chlorhexidine acetate, chlorhexidine gluconate, chlorhexidine hydrochloride, 1-phenoxy-propan-2-ol, N-alkyl($C_{12}$-$C_{22}$)trimethylammonium bromide and chloride, 4,4-dimethyl-1,3-oxazolidine, N-hydroxymethyl-N-(1,3-di(hydroxymethyl)-2,5-dioxoimidazolidin-4-yl)-N'-hydroxymethyl urea, 1,6-bis(4-amidino-phenoxy)-n-hexane and the salts thereof, glutaraldehyde, 5-ethyl-1-aza-3,7-dioxabicyclo(3.3.0)octane, 3-(4-chlorophenoxy)-1,2-propanediol, Hyamine, alkyl-($C_8$-$C_{18}$)dimethylbenzylammonium chloride, alkyl-($C_8$-$C_{18}$)-dimethylbenzylammonium bromide, alkyl-($C_8$-$C_{18}$)-dimethylbenzylammonium saccharinate, benzylhemiformal, 3-iodo-2-propynylbutyl carbamate, sodium hydroxymethylaminoacetate or sodium hydroxymethylaminoacetate.

Perfume Oils and Aromas

Polyethylene glycol esters of the formula 1 and in particular the preparations according to the invention containing at least one polyethylene glycol ester (preferably according to the invention) of the formula 1 and at least one polyethylene glycol ether of the formula 2 may also promote the solubility behavior of perfume oils and aromas in cosmetic and dermatological preparations. Perfume oils which may be mentioned are mixtures of natural and synthetic odoriferous substances. Natural odoriferous substances are for example extracts of blossoms (lily, lavender, rose, jasmine, neroli, ylang-ylang), stems and leaves (geranium, patchouli, petitgrain), fruits (aniseed, coriander, caraway, juniper), fruit peels (bergamot, lemon, orange), roots (mace, angelica, celery, cardamom, Costus, iris, Calmus), woods (stone pine, sandalwood, guaiac, cedar, rosewood), herbs and grasses (tarragon, lemongrass, sage, thyme), needles and branches (spruce, fir, pine, mountain pine), resins and balsams (galbanum, elemi, benzoin, myrrh, olibanum, opoponax). Animal raw materials are also feasible, such as for example civet and castoreum. Typical synthetic odoriferous substance compounds are products of the ester, ether, aldehyde, ketone, alcohol and hydrocarbon types. Odoriferous substance compounds of the ester type are for example benzyl acetate, phenoxyethyl isobutyrate, p-tert.-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether, the aldehydes include, for example, linear alkanals having 8 to 18 carbon atoms, citral, citronellal, citronellyloxyacetaldehyde, cyclamen aldehyde, hydroxycitronellal, lilial and bourgeonal, the ketones include, for example, ionones, alphaisomethyl ionone and methyl cedryl ketone, the alcohols include anethole, citronellol, eugenol, isoeugenol, geraniol, linalool, phenylethyl alcohol and terpineol, the hydrocarbons mainly include terpenes and balsams. Preferably, however, mixtures of various odoriferous substances which together produce an attractive fragrance note are used. Relatively low volatility essential oils, which are generally used as aroma components, are also suitable as perfume oils, for example sage oil, camomile oil, clove oil, melissa oil, mint oil, cinnamon leaf oil, lime blossom oil, juniper berry oil, vetiver oil, olibanum oil, galbanum oil, labolanum oil and lavandin oil. Preferably, bergamot oil, dihydromyrcenol, lilial, lyral, citronellol, phenylethyl alcohol, alpha-hexylcinnamaldehyde, geraniol, benzyl acetone, cyclamen aldehyde, linalool, Boisambrene Forte, ambroxan, indole, hedione, sandelice, lemon oil, mandarin oil, orange oil, allyl amyl glycolate, cyclovertal, lavandin oil, muscatel oil, sage oil, beta-damascone, geranium oil Bourbon, cyclohexyl salicylate, Vertofix Coeur, Iso E Super, Fixolide NP, evernyl, iraldein gamma, phenylacetic acid, geranyl acetate, benzyl acetate, rose oxide, romillatei, irotyl and floramate are used alone or in mixtures. Examples of possible aromas are peppermint oil, spearmint oil, anise oil, star anise oil, caraway oil, eucalyptus oil, fennel oil, lemon oil, wintergreen oil, clove oil, menthol and the like.

Dyes

Polyethylene glycol esters of the formula 1 and in particular the preparations according to the invention containing at least one polyethylene glycol ester (preferably according to the invention) of the formula 1 and at least one polyethylene glycol ether of the formula 2 may also promote the solubility behavior of dyes in cosmetic and dermatological preparations. Substances suitable and authorized for cosmetic purposes may be used as dyes. Examples are cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). Luminol may also be included as a luminescent dye. These dyes are conventionally used in concentrations of from 0.001 to 0.1 wt. %, relative to the total mixture.

Preferred developments and further aspects of the present invention are revealed by the attached claims and the following Examples. Unless otherwise stated, all stated values relate to weight.

EXAMPLES

Example 1

In Vivo Detection of the Effect of a Preparation According to the Invention Reducing Sodium Lauryl Sulfate-Induced Skin Drying, Said Preparation Containing a polyethylene glycol ester According to the Invention of 3,5,5-trimethylhexanoic acid (reaction of 1 mol of 3,5,5-trimethylhexanoic acid with 5 mol of ethylene oxide) and a Conventional Commercial polyethylene glycol ether of tridecanol (INCI name: Trideceth-9; CTFA monograph id 3247)

In order to investigate to what extent preparations according to the invention containing a polyethylene glycol ester of the formula 1 and a polyethylene glycol ether of the formula 2 may prevent drying of the skin during the washing process, caused by surfactant compounds such as sodium lauryl sulfate (INCI: Sodium Laureth Sulfate), human in vivo studies were carried out using different washing lotions. The water contents of the skin before and after treatment with washing lotion A containing pure water, washing lotion B containing defatting sodium lauryl sulfate and with washing lotion C containing defatting sodium lauryl sulfate and a preparation according to the invention consisting of PEG-5 isononanoate and trideceth-9 were determined by comparison. The exact amount ratios of the substances contained in washing lotions A, B and C are compared in Table 2.

TABLE 2

Qualitative and quantitative composition of washing lotions A, B and C

| INCI | Washing lotion A | Washing lotion B | Washing lotion C |
|---|---|---|---|
| Sodium Laureth Sulfate | — | 3.00 | 3.00 |
| Trideceth-9 | — | — | 3.05 |
| PEG mono/diester mixture (according to Table 1); reaction of 1 mol of 3,5,5-trimethylhexanoic with 5 mol of ethylene oxide (5 ethylene oxide units) | — | — | 1.45 |
| Water (Aqua) | 100.00 | 97.00 | 92.50 |
| Total | 100.00 | 100.00 | 100.00 |

The following experimental parameters were selected for the in vivo study:
Number of subjects: 19 female subjects in the age range from 30-65 years
Test surface: underside of forearm
Test duration: 7 days
Test areas: 3 test areas treated with washing lotions A, B and C
Application: 3× daily
Measurement of water content of skin by means of corneometry prior to start of treatment of skin and on 7th day, 3 hours after final application.

DETAILED DESCRIPTION OF EXPERIMENT

The effect of washing lotions A to C on skin moisture was determined by means of corneometry on female test subjects. Corneometry is a capacitive measurement method which exploits the fact that the dielectric constant of water differs markedly from that of most other substances. An appropriately shaped measuring capacitor (sensor) reacts, depending on water content, with variable changes in capacitance on skin fields to be investigated. These changes in capacitance of the sensor are processed fully automatically by the instrument to yield a digital measured value. No conductive (galvanic) connection exists between the measured object and the measuring instrument; for this reason, almost no current flows through the measured object. Characteristics such as ion conductivity and polarization effects have virtually no influence on the measurement result. The almost inertia-free "adaptation profile" of the electronics to the prevailing moisture conditions enables very rapid measurement and extensive elimination of any influence on the results arising from involuntary movements or moisture build-up during measurement.

In preparation, the test subjects were asked not to use any skin moisture-regulating cosmetics for at least 3 days before the start of the study. In addition, the test subjects were not allowed to use any further cleansing or conditioning products over the entire test period.

Directly before the start of the actual tests, the test subjects were acclimatized for 45 min to a room temperature of 22° C. (±1° C.) and 50% (±5%) relative atmospheric humidity. First of all, the initial skin moisture values were then measured in the 3 test fields. The initial values in the test fields were established for each subject (in each case 5 corneometer values per test field per subject).

Then washing emulsions A to C are applied according to test protocol 3 times daily (morning, midday, evening) for a period of 7 days. At the end of the test period, exactly 3 hours after the final application of test products on the 7th day, skin moisture is again measured using corneometry. The results are shown in Table 3. The stated delta values are averaged difference values between the respective product measured values on day 7 and the associated measured values of the respective measurement fields at time 0 prior to first application of the product.

Result:
The delta values for washing lotions A, B and C are shown in Table 3 in each case relative to the initial value.

TABLE 3

Skin moisture values determined by corneometry; comparison of delta values of washing lotions A, B and C

| Product | Mean values (19 test subjects) [CU] Cornemeter units Initial value [CU] (t = 0 days) | Mean values (19 test subjects) [CU] Cornemeter units Final value [CU] (t = 7 days) | Mean values (19 test subjects) [CU] Cornemeter units Delta values [CU] final value − initial value | Significance (t-test) (++) = significant; p = 0.05 (−−) = not significant p = 0.05 Comparison of final value with initial value |
|---|---|---|---|---|
| Washing lotion A | 34.8 | 35.0 | 0.2 | (−−) |

TABLE 3-continued

Skin moisture values determined by corneometry; comparison of delta values of washing lotions A, B and C

| Product | Mean values (19 test subjects) [CU] Cornemeter units Initial value [CU] (t = 0 days) | Mean values (19 test subjects) [CU] Cornemeter units Final value [CU] (t = 7 days) | Mean values (19 test subjects) [CU] Cornemeter units Delta values [CU] final value − initial value | Significance (t-test) (++) = significant; p = 0.05 (−−) = not significant p = 0.05 Comparison of final value with initial value |
|---|---|---|---|---|
| Washing lotion B | 35.2 | 32.4 | −2.8 | (++) |
| Washing lotion C | 35.1 | 34.7 | −0.4 | (−−) |

As the measurements of the skin moisture situation made using corneometry show, when washing lotion B is applied a considerable, statistically significant reduction in skin moisture of 2.8 corneometer units occurs as a result of the defatting properties of sodium lauryl sulfate (INCI name: Sodium Laureth Sulfate) over the 7 day test period. In the case of washing lotion A, containing only water, on the other hand, no statistically significant reduction in water content was measured relative to the test field at time t=0 days. In the case of washing lotion C, containing sodium lauryl sulfate and a preparation according to the invention consisting of the polyethylene glycol ester according to the invention of 3,5,5-trimethylhexanoic acid (reaction of 1 mol of 3,5,5-trimethylhexanoic acid with 5 mol of ethylene oxide) and trideceth-9, it was likewise impossible to detect any statistically significant reduction in water content over the test period compared with the test field at time t=0 days. It has thus been unambiguously demonstrated that the mixtures according to the invention containing at least one polyethylene glycol ester according to the invention of the formula 1 and at least one polyethylene glycol ether of the formula 2 may prevent drying out of the skin during the washing process caused by surfactant compounds such as sodium lauryl sulfate and thus counteract to an excellent degree the associated disadvantages such as erythema of the skin and scalp, pruritus and dandruff.

Example 2

Cosmetic Formulations Containing a Preparation According to the Invention Consisting of a polyethylene glycol ester According to the Invention of 3,5,5-trimethylhexanoic acid (reaction of 1 mol of 3,5,5-trimethylhexanoic acid with 5 mol of ethylene oxide) and a polyethylene glycol ether of tridecanol (INCI Name: Trideceth-9; CTFA Monograph Id 3247)

Cosmetic and dermatological formulations are listed below which, due to their content of preparations according to the invention containing at least one polyethylene glycol ester of the formula 1 and at least one polyethylene glycol ether of the formula 2, may preferably be used to cleanse and condition skin and to prevent surfactant-based drying out of the skin.

| Ingredients | INCI name | % wt./wt. | | | | | |
|---|---|---|---|---|---|---|---|
| | | 1 | 2 | 3 | 4 | 5 | 6 |
| PEG-9 Tridecylether | Trideceth-9 | 0.61 | 1.22 | 0.61 | 0.29 | 0.68 | 3.05 |
| PEG mono/diester mixture (according to Table 1); reaction of 1 mol of 3,5,5-trimethylhexanoic acid with 5 mol of ethylene oxide (5 ethylene oxide units) | | 0.29 | 0.58 | 0.29 | 0.61 | 0.68 | 1.45 |
| (−) alpha bisabolol | Bisabolol | | | | | | 0.2 |
| Allantoin | Allantoin | 0.1 | | | | | |
| Aloe vera gel concentrate 10/1 | Aloe Barbadensis Leaf Juice | 1.0 | | | | | |
| Arlypon F | Laureth-2 | | | | | 2.0 | |
| Carbopol Ultrez 10 | Carbomer | | | 0.5 | | | |
| Carbopol Ultrez 21 | Acrylates/C10-30 Alkyl Acrylate Crosspolymer | 0.4 | | | | | |
| Cholesterol | Cholesterol | | | | | | 0.1 |
| Citric acid 10% | Citric Acid | | | | | 0.5 | |
| Caffeine | Caffeine | | 0.1 | | | | |
| Crinipan AD | Climbazole | | | | | 0.3 | |
| Dehyton K | Cocamidopropyl Betaine | | | | | 10.0 | 8.0 |
| Deolite | Pentylene Glycol, Dimethyl Phenylpropanol | | | | | | |

-continued

| Trade name | INCI | 1 | 2 | 3 | 4 | 5 | 6 |
|---|---|---|---|---|---|---|---|
| D-Pantenol 75 L | Panthenol | 0.5 | | | | 0.5 | |
| Drago-Beta-Glucan | Water (Aqua), Butylene Glycol, Glycerin, *Avena Sativa* (Oat) Kernel Extract | | 0.5 | | | | |
| DragoCalm | Water, Glycerin, *Avena Sativa* (Oat Kernel Extract) | | | 1.0 | | | |
| Dragocare W | PEG-40 Butyloctanol Wheat Germ Esters, Water, Lactic Acid, Tocopherol | | | | | | |
| Dragocid Liquid | Phenoxyethanol, Methylparaben, Ethylparaben, Butylparaben, Propylparaben, Isobutylparaben | | | | 0.8 | 0.7 | |
| Dragoderm | Glycerin, *Triticum Vulgare* (Wheat) Gluten, Water (Aqua) | | | | | | |
| Dragosantol 100 | Bisabolol | | | | | | |
| Dragoxat 89 | Ethylhexyl Isononanoate | | | 2.0 | | | |
| EDTA BD | Disodium EDTA | | | | | | |
| Ethanol 96% | Alcohol Denat. | 8.0 | 15.0 | 15.0 | | | |
| Eumulgin EO33 | PEG-150 Distearate | | | | | | |
| Extrapon Aloe Vera | Water (Aqua), *Aloe Barbadensis* Leaf Extract, Propylene Glycol, Alcohol | | | | | | |
| Extrapon Guarana | Water (Aqua), Propylene Glycol, *Paullinia Cupana* Seed Extract, Alcohol | | 2.0 | | | 0.5 | |
| Extrapon Chamomile | Water (Aqua), Propylene Glycol, Butylene Glycol, *Chamomilla Recutita* (*Matricaria*) Flower Extract, Bisabolol | | | | | | |
| Extrapon Lemon Grass | Propylene Glycol, Water (Aqua), PEG-40 Hydrogenated Castor Oil, Trideceth-9, *Cymbopogon Citratus* Leaf Oil, Lactic Acid | | | | | | 1.0 |
| Farnesol | Farnesol | | | | | | |
| Frescolat MGA | Menthone Glycerin Acetal | | | | | | |
| Frescolat ML | Menthyl Lactate | 0.3 | 0.3 | | | 0.2 | |
| Fruitapone Orange B | Propylene Glycol, Water (Aqua), Citric Acid, Citrus *Aurantium Dulcis* (Orange) Juice, Trideceth-9, Bisabolol | | | | | | 1.0 |
| Genapol LRO Liquid | Sodium Laureth Sulfate | | | | 25.0 | | |
| Glycerol 99.5 P | Glycerol | | | 2.0 | | | |
| Hydrolite-5 | Pentylene Glycol | 5.0 | | | | | |
| Hydroviton-24 | Water, Pentylene Glycol, Glycerin, Lactic Acid, Sodium Lactate, Serine, Urea, Sorbitol, Sodium Chloride, Allantoin | 0.5 | 1.0 | | | | |
| Iso Adipat | Diisopropyl Adipate | | | | | | |
| Isodragol | Triisononanoin | | | | | | |
| Isopropanol | Isopropyl Alcohol | | | | | | 45.0 |
| Lime blossom distillate | Water (Aqua), Alcohol, *Tilia Cordata* Flower Water | | | | 1.0 | | |
| Merquat 550 | Polyquaternium-7 | | | | | | |
| Sodium benzoate | Sodium Benzoate | | | | | | |
| Sodium chloride | Sodium Chloride | | | | 2.5 | 0.1 | |
| Sodium hydroxide 10% soln. | Sodium Hydroxide | 0.7 | 1.6 | | | | 0.1 |
| Oxetal VD 92 | PEG-90 Glyceryl Isostearate, Laureth-2 | | | | | | |
| Panthenol | | | | | | | |
| Perfume oil | Fragrance | 0.1 | 0.2 | 0.1 | 0.3 | 0.5 | 0.1 |
| PCL Liquid 100 | Cetearyl Ethylhexanoate | | | | | | 0.1 |
| Polymer JR 400 | Polyquaternium-10 | | | | | 0.4 | |
| 1,2-propylene glycol | Propylene Glycol | 5.0 | 5.0 | | | | |
| Rewomid C212 | Cocamide MEA | | | | | | |
| Sepigel 305 | Polyacrylamide, C13-14 Isoparaffin, Laureth-7 | | | 4.0 | | | |

| Ingredients | INCI name | | | | | | |
|---|---|---|---|---|---|---|---|
| Setacin 103 special | Disodium Laureth Sulfosuccinate | | | | | | |
| Solubilizer | PEG-40 Hydrogenated Castor Oil, Trideceth-9, Propylene Glycol, Water (Aqua) | 1.5 | 1.2 | | | | |
| SymClariol | Decylene Glycol | | | | | | 0.5 |
| SymDeo MPP | Dimethyl Phenyl 2-Butanol | | | | | | |
| Symdiol 68 | 1,2-Hexanediol, Caprylyl Glycol | | | | 0.5 | | |
| Symdiol 68T | 1,2-Hexanediol, Caprylyl Glycol, Tropolone | | | | | | |
| SymGlucan | Water (Aqua), Glycerin, Beta-Glucan | | | | | | |
| SymRelief | Bisabolol, *Zingiber Officinale* (Ginger) Root Extract | 0.2 | | | | 0.2 | |
| SymRepair | Hexyldecanol, Bisabolol, Cetylhydroxy-proline Palmitamide, Stearic Acid, *Brassica Campestris* (Rapeseed Sterols) | | | 0.5 | | | |
| Tego Betaine L7 | Cocamidopropyl Betaine | | | | | | |
| Texapon70 | Sodium Laureth Sulfate | | | | | | |
| Texapon NSO | Sodium Laureth Sulfate | | | | | 37.0 | |
| Water | Water (Aqua) | To make up to 100 | To make up to 100 | To make up to 100 | To make up to 100 | To make up to 100 | To make up to 100 |

| | | % wt./wt. | | | | | |
|---|---|---|---|---|---|---|---|
| Ingredients | INCI name | 7 | 8 | 9 | 10 | 11 | 12 |
| PEG-9 Tridecylether | Trideceth-9 | 1.83 | 1.35 | 1.16 | 0.61 | 0.61 | 0.29 |
| PEG mono/diester mixture (according to Table 1); reaction of 1 mol of 3,5,5-trimethylhexanoic acid with 5 mol of ethylene oxide (5 ethylene oxide units) | | 0.87 | 1.35 | 2.44 | 0.29 | 0.29 | 0.61 |
| (−) alpha bisabolol | Bisabolol | | | | | | |
| Allantoin | Allantoin | | | | 0.1 | | 0.1 |
| Aloe vera gel concentrate 10/1 | *Aloe Barbadensis* Leaf Juice | | | | 0.5 | | |
| Arlypon F | Laureth-2 | | | | | | |
| Carbopol Ultrez 10 | Carbomer | | | 0.5 | | | |
| Carbopol Ultrez 21 | Acrylates/C10-30 Alkyl Acrylate Crosspolymer | | | | | | |
| Cholesterol | Cholesterol | | | | | | |
| Citric acid 10% | Citric Acid | | | | | 0.3 | 0.3 |
| Caffeine | Caffeine | | | | | | |
| Crinipan AD | Climbazole | | | | | | |
| Dehyton K | Cocamidopropyl Betaine | | | | | | |
| Deolite | Pentylene Glycol, Dimethyl Phenylpropanol | | | | | | 1.0 |
| D-Pantenol 75 L | Panthenol | | | | | | |
| Drago-Beta-Glucan | Water (Aqua), Butylene Glycol, Glycerin, *Avena Sativa* (Oat) Kernel Extract | | | | | | 1.0 |
| DragoCalm | Water, Glycerin, *Avena Sativa* (Oat Kernel Extract) | | | | | | |
| Dragocare W | PEG-40 Butyloctanol Wheat Germ Esters, Water, Lactic Acid, Tocopherol | 1.0 | | | | | |
| Dragocid Liquid | Phenoxyethanol, Methylparaben, Ethylparaben, | 0.8 | | | | | |

| | | | | | | | |
|---|---|---|---|---|---|---|---|
| | Butylparaben, Propylparaben, Isobutylparaben | | | | | | |
| Dragoderm | Glycerin, *Triticum Vulgare* (Wheat) Gluten, Water (Aqua) | | | | 1.0 | | |
| Dragosantol 100 | Bisabolol | 0.1 | | | | | |
| Dragoxat 89 | Ethylhexyl Isononanoate | | | | | | |
| EDTA BD | Disodium EDTA | | | | 0.1 | | |
| Ethanol 96% | Alcohol Denat. | | | | | | 20.0 |
| Eumulgin EO33 | PEG-150 Distearate | | | | | 0.6 | |
| Extrapon *Aloe Vera* | Water (Aqua), *Aloe Barbadensis* Leaf Extract, Propylene Glycol, Alcohol | | 0.5 | | | | |
| Extrapon Guarana | Water (Aqua), Propylene Glycol, *Paullinia Cupana* Seed Extract, Alcohol | | | | | | |
| Extrapon Chamomile | Water (Aqua), Propylene Glycol, Butylene Glycol, *Chamomilla Recutita* (*Matricaria*) Flower Extract, Bisabolol | | | 1.0 | | | |
| Extrapon Lemon Grass | Propylene Glycol, Water (Aqua), PEG-40 Hydrogenated Castor Oil, Trideceth-9, *Cymbopogon Citratus* Leaf Oil, Lactic Acid | | | | | | |
| Farnesol | Farnesol | | | | 0.3 | | |
| Frescolat MGA | Menthone Glycerin Acetal | | | | 0.3 | | |
| Frescolat ML | Menthyl Lactate | | | | | | |
| Fruitapone Orange B | Propylene Glycol, Water (Aqua), Citric Acid, Citrus *Aurantium Dulcis* (Orange) Juice, Trideceth-9, Bisabolol | | | | | | |
| Genapol LRO Liquid | Sodium Laureth Sulfate | | | | | | |
| Glycerol 99.5 P | Glycerol | | 5.0 | | | | |
| Hydrolite-5 | Pentylene Glycol | | | 5.0 | | 3.0 | 3.0 |
| Hydroviton-24 | Water, Pentylene Glycol, Glycerin, Lactic Acid, Sodium Lactate, Serine, Urea, Sorbitol, Sodium Chloride, Allantoin | | | | | | |
| Iso Adipat | Diisopropyl Adipate | | 0.5 | | | | 0.2 |
| Isodragol | Triisononanoin | | | | | | 0.2 |
| Isopropanol | Isopropyl Alcohol | | | | | | |
| Lime blossom distillate | Water (Aqua), Alcohol, *Tilia Cordata* Flower Water | | | | | | |
| Merquat 550 | Polyquaternium-7 | | | | 0.5 | | |
| Sodium benzoate | Sodium Benzoate | | | | 0.5 | | |
| Sodium chloride | Sodium Chloride | | | | 1.0 | 1.2 | 1.2 |
| Sodium hydroxide 10% soln. | Sodium Hydroxide | | | 1.0 | | | |
| Oxetal VD 92 | PEG-90 Glyceryl Isostearate, Laureth-2 | 3.0 | | | | | |
| Panthenol | | 0.5 | 0.5 | | | | |
| Perfume oil | Fragrance | 0.5 | 0.1 | 0.2 | 0.5 | 0.4 | 1.0 |
| PCL Liquid 100 | Cetearyl Ethylhexanoate | | | | | | |
| Polymer JR 400 | Polyquaternium-10 | | | | | | |
| 1,2-propylene glycol | Propylene Glycol | | 5.0 | | | | |
| Rewomid C212 | Cocamide MEA | | | | 0.5 | | |
| Sepigel 305 | Polyacrylamide, C13-14 Isoparaffin, Laureth-7 | | | | | | |
| Setacin 103 special | Disodium Laureth Sulfosuccinate | 25.0 | | | | | |
| Solubilizer | PEG-40 Hydrogenated Castor Oil, Trideceth-9, Propylene Glycol, Water (Aqua) | 0.8 | 1.0 | 0.2 | | | 1.0 |
| SymClariol | Decylene Glycol | | | | | | |
| SymDeo MPP | Dimethyl Phenyl 2-Butanol | | | | 1.0 | | |
| Symdiol 68 | 1,2-Hexanediol, Caprylyl Glycol | | | | | | |

| | | | | | | | |
|---|---|---|---|---|---|---|---|
| Symdiol 68T | 1,2-Hexanediol, Caprylyl Glycol, Tropolone | 0.5 | | | | | |
| SymGlucan | Water (Aqua), Glycerin, Beta-Glucan | 1.0 | | | | | |
| SymRelief | Bisabolol, *Zingiber Officinale* (Ginger) Root Extract | | | | | | |
| SymRepair | Hexyldecanol, Bisabolol, Cetylhydroxy-proline Palmitamide, Stearic Acid, *Brassica Campestris* (Rapeseed Sterols) | | | | | | |
| Tego Betaine L7 | Cocamidopropyl Betaine | 11.0 | | | 6.0 | 8.0 | |
| Texapon70 | Sodium Laureth Sulfate | | | | | 22.0 | |
| Texapon NSO | Sodium Laureth Sulfate | | | 37.0 | | | |
| Water | Water (Aqua) | To make up to 100 | To make up to 100 | To make up to 100 | To make up to 100 | To make up to 100 | To make up to 100 |

1 = Aftershave hydro gel
2 = Anticellulite gel
3 = Aftershave lotion
4 = Washing lotion
5 = Antidandruff shampoo
6 = Antiacne wipe
7 = Mild shampoo
8 = Face gel
9 = Face lotion
10 = Shower gel
11 = Crystal-clear shampoo
12 = Deo pump spray

SPECIFIC EMBODIMENTS

Specific embodiment one is polyethylene glycol esters of the formula 1

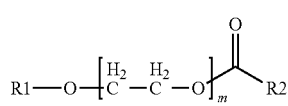

Formula 1 wherein m=3 to 7, $R_1$=H or

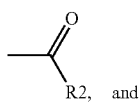

$R_2$=in each case a branched or unbranched alkyl group, whose number of carbon atoms amounts to 8, apart from CARN 127739-58-6, 7339-81-3, 7339-80-2 and 31621-91-7.

Specific embodiment two is the polyethylene glycol esters as in specific embodiment one, characterized in that m amounts to 5.

Specific embodiment three is a cosmetic and/or dermatological preparation containing one or more polyethylene glycol esters of the formula 1

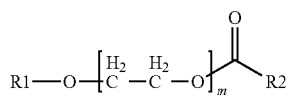

wherein m=3 to 7, $R_1$=H or

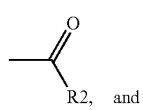

$R_2$=in each case a branched or unbranched alkyl group, whose number of carbon atoms amounts to 8.

Specific embodiment four is a preparation containing a polyethylene glycol ester of the formula 1

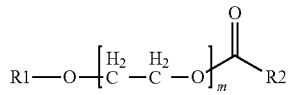

wherein m=3 to 7, $R_1$=H or

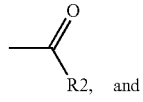

$R_2$=in each case a branched or unbranched alkyl group, whose number of carbon atoms amounts to 8, and one or more polyethylene glycol ethers of the formula 2,

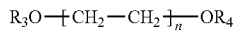

Formula 2 wherein n=7 to 30, and $R_3$ and $R_4$ in each case, mutually independently, mean H or a saturated or unsaturated, branched or unbranched alkyl group, in which the number of carbon atoms amounts to 10-15.

Specific embodiment five is the preparation as in specific embodiment four, characterized in that n amounts, in one or more polyethylene glycol ethers of the formula 2, to 9 and $R_3$ and/or $R_4$ mean a saturated or unsaturated, branched or unbranched alkyl group, in which the number of carbon atoms amounts to 13.

Specific embodiment six is the preparation as in one of specific embodiments four to five, characterized in that the ratio of the total mass of all polyethylene glycol esters of the formula 1, in which only one of the residues $R_1$ and $R_2$ is H, to the total mass of all polyethylene glycol esters of the formula 1, in which the residues $R_1$ and $R_2$ are not H, is 4:1 to 1:3, preferably 3:1 to 1:2 and most preferably 2:1 to 1:1.

Specific embodiment seven is the preparation as in one of specific embodiments three to four, containing the polyethylene glycol ester(s) of the formula 1 in a sufficient concentration a) to condition the skin, and/or b) to reduce, delay or prevent drying out of the skin, and/or c) to regenerate the skin barrier function, and/or d) to moisturize the skin.

Specific embodiment eight is the preparation as in one of specific embodiment specific embodiments four to seven, wherein the preparation is a water-containing preparation, and containing the polyethylene glycol ether of the formula 2 in a sufficient concentration to increase the solubility of one or more polyethylene glycol esters of the formula 1 in the preparation.

Specific embodiment nine is the preparation as in one of specific embodiments three to eight, characterized in that m amounts, in one or more of the polyethylene glycol esters of the formula 1, to 5.

Specific embodiment ten is the preparation as in one of specific embodiments three to nine, characterized in that the preparation is a water-containing preparation with a surfactant content of 2-30 wt. % relative to the total preparation.

Specific embodiment eleven is a method of producing a polyethylene glycol ester of the formula 1

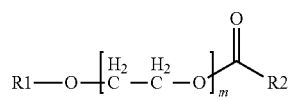

Formula 1 wherein m=3 to 7, $R_1$=H or

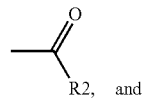

$R_2$, and $R_2$=in each case a branched or unbranched alkyl group, whose number of carbon atoms amounts to 8, comprising reacting ethylene oxide with one or a mixture comprising a plurality of saturated or unsaturated, branched or unbranched alkyl carboxylic acids, whose number of carbon atoms amounts to 9.

Specific embodiment twelve is the method as in specific embodiment eleven, wherein the carboxylic acid is selected from 3,5,5-trimethylhexanoic acid, isononanoic acid and a mixture of the two carboxylic acids.

Specific embodiment thirteen is the preparation as in one of specific embodiments three to ten, characterized in that the content of polyethylene glycol esters of the formula 1 and/or the content of polyethylene glycol ethers of the formula 2 amounts in each case to 0.01-50 wt. % relative to the total preparation, with the proviso that the total content of polyethylene glycol esters of the formula 1 and polyethylene glycol ethers of the formula 2 amounts to no more than 50 wt. %.

Specific embodiment fourteen is the preparation as in one of specific embodiments four to ten or thirteen, characterized in that the amount ratio of polyethylene glycol esters of the formula 1 to polyethylene glycol ethers of the formula 2 amounts to 90:10 to 10:90 and preferably to 75:25 to 25:75.

Specific embodiment fifteen is the preparation as in one of specific embodiments three to ten or thirteen to fourteen, further containing one or more moderately water-soluble active ingredients selected from the group consisting of odoriferous substances, perfume oils, aroma substances, aromas, fatty oils, fatty acids, waxes, ceramides, pseudoceramides, sterols, phytosterols, antiacne active ingredients, antidandruff active ingredients, antimicrobial active ingredients, preservatives, antiperspirants, antiirritants, pruritus-relieving active ingredients, cooling active ingredients, antioxidants, UV filters, antiaging active ingredients, skin-lightening and skin-tanning active ingredients, skin moisture regulators, osmolytes, insect repellents, enzyme inhibitors, odor absorbers, dyes.

Specific embodiment sixteen is the preparation as in one of specific embodiments three to ten or thirteen to fifteen, wherein the preparation is a preparation of the surfactant cleansing product type, such as shampoo, shower gel or bath preparation, of the "water-in-oil" (W/O) type, of the "oil-in-water" (O/W) or multiple emulsions, in particular of the water-in-oil-in-water (W/O/W), PIT emulsion, Pickering emulsion, microemulsion or nanoemulsion type.

Specific embodiment seventeen is use of a polyethylene glycol ester of the formula 1

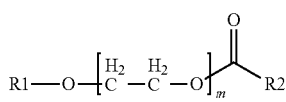

Formula 1 wherein m=3 to 7, $R_1$=H or

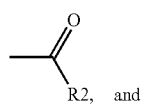

$R_2$ = in each case a branched or unbranched alkyl group, whose number of carbon atoms amounts to 8, and/or a preparation as in one of specific embodiments three to ten or thirteen to sixteen,
 a) to condition the skin, and/or
 b) to reduce, delay or prevent drying out of the skin, and/or
 c) to regenerate the skin barrier function, and/or
 d) to moisturize the skin and/or
 e) in cosmetic and/or dermatological preparations.

Specific embodiment eighteen is use of a polyethylene glycol ester of the formula 2

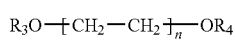

Formula 2 wherein n=7 to 30, and $R_3$ and $R_4$ in each case, mutually independently, mean H or a saturated or unsaturated, branched or unbranched alkyl group, in which the number of carbon atoms amounts to 10 to 15,
 a) to increase the solubility of a polyethylene glycol ester of the formula 1 in a water-containing preparation and/or
 b) to increase the solubility of further moderately water-soluble cosmetic and dermatological active ingredients.

The invention claimed is:

1. A cosmetic and/or dermatological preparation comprising one or more polyethylene glycol esters of the formula 1

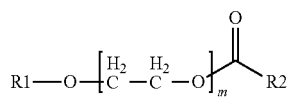

Formula 1 wherein m=5, $R_1$=H or

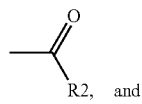

$R_2$ =

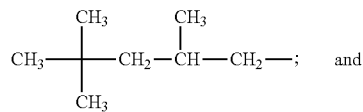

further comprising one or more polyethylene glycol ethers of the formula 2,

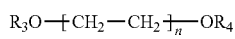

Formula 2 wherein n=7 to 30, and $R_3$ and $R_4$ in each case, mutually independently, mean H or a saturated or unsaturated, branched or unbranched alkyl group, in which the number of carbon atoms amounts to 10-15.

2. The preparation as claimed in claim 1, containing the polyethylene glycol ester(s) of claim 1 in a sufficient concentration
 a) to condition the skin, and/or
 b) to reduce, delay or prevent drying out of the skin, and/or
 c) to regenerate the skin barrier function, and/or
 d) to moisturize the skin.

3. A method
 a) to condition the skin, and/or
 b) to reduce, delay or prevent drying out of the skin, and/or
 c) to regenerate the skin barrier function, and/or
 d) to moisturize the skin,
comprising application of a cosmetic and/or dermatological preparation as claimed in claim 1.

4. The preparation as claimed in claim 1, characterized in that
 n amounts, in one or more polyethylene glycol ethers of the formula 2, to 9 and
 $R_3$ and/or $R_4$ mean a saturated or unsaturated, branched or unbranched alkyl group, in which the number of carbon atoms amounts to 13.

5. The preparation as claimed in claim 1, characterized in that the ratio of the total mass of all polyethylene glycol esters of claim 1, in which the residue $R_1$ is H, to the total mass of all polyethylene glycol esters of claim 1, in which the residue $R_1$ is not H, is 4:1 to 1:3.

6. The preparation as claimed in claim 1, wherein the preparation is a water-containing preparation, and containing the polyethylene glycol ether of the formula 2 in a sufficient concentration to increase the solubility of one or more polyethylene glycol esters of claim 1 in the preparation.

7. The preparation as claimed in claim 1, further characterized in that the preparation is a water-containing preparation with a surfactant content of 2-30 wt. % relative to the total preparation.

8. The preparation as claimed in claim 1, characterized in that the content of said polyethylene glycol esters amounts in each case to 0.01-50 wt. % relative to the total preparation.

9. The preparation as claimed in claim 1, characterized in that the amount ratio of polyethylene glycol esters of claim 1 to polyethylene glycol ethers of the formula 2 amounts to 90:10 to 10:90.

10. The preparation as claimed in claim 1, further containing one or more moderately water-soluble active ingredients selected from the group consisting of odoriferous substances, perfume oils, aroma substances, aromas, fatty oils, fatty acids, waxes, ceramides, pseudoceramides, sterols, phytosterols, antiacne active ingredients, antidandruff active ingredients, antimicrobial active ingredients, preservatives, antiperspirants, antiirritants, pruritus-relieving active ingredients, cooling active ingredients, antioxidants, UV filters, antiaging active ingredients, skin-lightening and skin-tanning active ingredients, skin moisture regulators, osmolytes, insect repellents, enzyme inhibitors, odor absorbers and dyes.

11. The preparation as claimed in claim 1, wherein the preparation is a preparation of the surfactant cleansing product type.

12. The preparation as claimed in claim 5, wherein the ratio is 3:1 to 1:2.

13. The preparation as claimed in claim 1, characterized in that the content of polyethylene glycol esters of claim 1 and/or the content of polyethylene glycol ethers of the formula 2 amounts in each case to 0.01-50 wt. % relative to the total preparation, with the proviso that the total content of polyethylene glycol esters of claim 1 and polyethylene glycol ethers of the formula 2 amounts to no more than 50 wt. %.

14. The preparation as claimed in claim 11, wherein the surfactant cleansing product type is selected from the group consisting of shampoo, shower gel and bath preparation, or selected from the group consisting of the "water-in-oil" (W/O) type, the "oil-in-water" (O/W) and multiple emulsions.

15. The preparation as claimed in claim 14, wherein the multiple emulsions are selected from the group consisting of the water-in-oil-in-water (W/O/W), PIT emulsion, Pickering emulsion, microemulsion and nanoemulsion types.

* * * * *